(12) United States Patent
Huang et al.

(10) Patent No.: US 10,973,764 B2
(45) Date of Patent: Apr. 13, 2021

(54) NEUROPROTECTIVE LIPOSOME COMPOSITIONS AND METHODS FOR TREATMENT OF STROKE

(71) Applicant: The Board of Regents of The University of Texas System, Austin, TX (US)

(72) Inventors: Shao-Ling Huang, Houston, TX (US); Melvin E. Klegerman, Houston, TX (US); Yong-Jian Geng, Houston, TX (US); Hyunggun Kim, Houston, TX (US); David D. Mcpherson, Houston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/453,252

(22) Filed: Jun. 26, 2019

(65) Prior Publication Data

US 2020/0101015 A1   Apr. 2, 2020

Related U.S. Application Data

(63) Continuation of application No. 14/420,429, filed as application No. PCT/US2013/054349 on Aug. 9, 2013, now Pat. No. 10,369,103.

(60) Provisional application No. 61/682,130, filed on Aug. 10, 2012.

(30) Foreign Application Priority Data

Sep. 21, 2012  (CN) .......................... 2012 1 0356929

(51) Int. Cl.
| A61K 9/127 | (2006.01) |
| A61K 33/00 | (2006.01) |
| A61K 9/00 | (2006.01) |
| A61K 41/00 | (2020.01) |

(52) U.S. Cl.
CPC ............ *A61K 9/127* (2013.01); *A61K 9/0019* (2013.01); *A61K 33/00* (2013.01); *A61K 41/0028* (2013.01)

(58) Field of Classification Search
None
See application file for complete search history.

(56) References Cited

U.S. PATENT DOCUMENTS

| 5,013,556 A | * | 5/1991 | Woodle | ................ A61K 9/1271 424/450 |
| 5,228,446 A | | 7/1993 | Unger et al. | |
| 5,498,421 A | | 3/1996 | Grinstaff et al. | |
| 5,612,057 A | | 3/1997 | Lanza et al. | |
| 5,639,441 A | | 6/1997 | Sievers et al. | |
| 5,670,177 A | | 9/1997 | Briend | |
| 5,769,080 A | | 6/1998 | Unger | |
| 5,853,752 A | | 12/1998 | Unger et al. | |
| 5,858,399 A | | 1/1999 | Lanza et al. | |
| 6,050,444 A | | 4/2000 | Sugg | |
| 6,123,919 A | | 9/2000 | Albert et al. | |
| 6,241,966 B1 | | 6/2001 | Albert et al. | |
| 6,274,633 B1 | | 8/2001 | Franks | |
| 6,443,898 B1 | | 9/2002 | Unger et al. | |
| 6,559,190 B1 | | 5/2003 | Petzelt | |
| 6,576,220 B2 | | 6/2003 | Unger | |
| 6,653,354 B2 | | 11/2003 | Franks | |
| 7,235,264 B2 | | 6/2007 | Neu et al. | |
| 7,390,508 B2 | | 6/2008 | Franks | |
| 7,405,241 B2 | | 7/2008 | Lemaire | |
| 7,442,383 B2 | | 10/2008 | Franks | |
| 7,632,872 B2 | | 12/2009 | Franks | |
| 7,700,135 B2 | | 4/2010 | Neu et al. | |
| 7,976,743 B2 | | 7/2011 | Huang et al. | |
| 8,143,317 B2 | | 3/2012 | Petzelt | |
| 10,369,103 B2 | | 8/2019 | Huang et al. | |
| 2001/0031243 A1 | | 10/2001 | Unger | |
| 2002/0052573 A1 | | 5/2002 | Georgieff | |
| 2003/0039613 A1 | | 2/2003 | Unger et al. | |
| 2003/0180375 A1 | | 9/2003 | Petzelt | |
| 2004/0166064 A1 | | 8/2004 | Gilkerson et al. | |
| 2005/0255169 A1 | | 11/2005 | Pilger et al. | |
| 2008/0175893 A1 | | 7/2008 | Huang et al. | |
| 2008/0187605 A1 | | 8/2008 | Olney | |
| 2008/0305156 A1 | | 12/2008 | Laing et al. | |
| 2009/0041833 A1 | | 2/2009 | Hettinger et al. | |
| 2009/0110643 A1 | | 4/2009 | Maruyama et al. | |

(Continued)

FOREIGN PATENT DOCUMENTS

| CN | 1668315 | 9/2005 |
| DE | 199 33 704 | 1/2001 |

(Continued)

OTHER PUBLICATIONS

Tiukinhoy-Liang et al (Thrombosis Research, 2007, 119, 777-784) (Year: 2007).*
David et al (The FASEB Journal, 22, 2008, 1275-1286) (Year: 2008).*
Demos et al (Journal of the American College of Cardiology, 33, 3, 1999, 867-857). (Year: 1999).*
Madani et al (Journal of Biophysics, 2011, Article ID 414729, 10 pages). (Year: 2011).*

(Continued)

*Primary Examiner* — Celeste A Roney
(74) *Attorney, Agent, or Firm* — Parker Highlander PLLC

(57) ABSTRACT

Methods for the treatment of stroke, such as stroke of undetermined origin, by administration of xenon (Xe)-loaded liposome compositions are provided. In some aspects, Xe is encapsulated in echogenic liposomes and release of Xe can be enhanced by application of ultrasound stimulation. Compositions for use in treating stroke, such as liposomes loaded with Xe or Xe in combination with H2 or H2S, are also provided.

4 Claims, 17 Drawing Sheets

(56) References Cited

U.S. PATENT DOCUMENTS

| | | |
|---|---|---|
| 2009/0311340 A1 | 12/2009 | Franks |
| 2010/0196461 A1 | 8/2010 | Simpkins |
| 2010/0278942 A1 | 11/2010 | Abraini |
| 2010/0291056 A1 | 11/2010 | Mosher et al. |
| 2010/0316729 A1 | 12/2010 | Franks et al. |
| 2011/0027378 A1 | 2/2011 | Pendharkar et al. |
| 2011/0104052 A1 | 5/2011 | Barnett et al. |
| 2011/0176994 A1 | 7/2011 | Pratt et al. |
| 2011/0177159 A1 | 7/2011 | Wu |
| 2011/0250183 A1 | 10/2011 | Picard et al. |
| 2012/0045528 A1 | 2/2012 | Bessiere |
| 2012/0087956 A1 | 4/2012 | Simpkins |
| 2013/0039993 A1 | 2/2013 | Lemaire |

FOREIGN PATENT DOCUMENTS

| | | |
|---|---|---|
| DE | 103 28 272 | 1/2004 |
| DE | 103 36 768 | 2/2004 |
| DE | 103 36 778 | 2/2004 |
| EP | 1 160 018 | 1/2002 |
| EP | 0 677 332 | 2/2002 |
| EP | 1 187 635 | 2/2004 |
| EP | 0 616 508 | 9/2004 |
| EP | 1 228 770 | 7/2005 |
| EP | 1 994 935 | 11/2008 |
| EP | 1 499 329 | 5/2012 |
| IT | MI20071031 | 11/2008 |
| JP | 2005-513417 | 5/2005 |
| JP | 2011-506432 | 3/2011 |
| WO | WO 2001/008692 | 2/2001 |
| WO | WO 2002/045721 | 6/2002 |
| WO | WO 2003/024306 | 3/2003 |
| WO | WO 03/105871 | 12/2003 |
| WO | WO 2005/067945 | 7/2005 |
| WO | WO 2006/126244 | 11/2006 |
| WO | WO 2009/075582 | 6/2009 |
| WO | WO 2012/020030 | 2/2012 |
| WO | WO 2012/096697 | 7/2012 |

OTHER PUBLICATIONS

Buchanan et al (J Pharm Sci, 2008, 97, 6, 2242-2249) (Year: 2008).*
"Ischemic versus hemorrhagic stroke", https://acls.com/free-resources/stroke/ischemic-versus-hemorrhagic-stroke, downloaded Sep. 7, 2016.
"Mobile Stroke Unit", http://my.clevelandclinic.org/services/neurologicalinstitute/cerebrovascularcenter/treatment-services/mobile-stroke-unit, downloaded Sep. 7, 2016.
"Stroke management and the impact of mobile stroke treatment units", http://alumni.clevelandclinic.org/index.php/ccjm-blog/J01-stroke-management-and-theimpact-of-mobile-stroke-treatment-units, downloaded Sep. 7, 2016.
"Stroke Treatments", http://www.healthline.com/health/stroke/treatments, downloaded Sep. 7, 2016.
Ardizzone, T. et al., "Glutamate Receptor Blockade Attenuates Glucose Hypermetabolism in Perihematomal Brain after Experimental Intracerebral Hemorrhage in Rat," Stroke 35(11):2587-91, 2004.
Britton et al., "In vivo therapeutic gas delivery for neuroprotection with echogenic liposomes", Circulation, 122(16): 1578-1587, 2010.
David et al., "Xenon is an inhibitor of tissue-plasminogen activator: adverse and beneficial effects in a rat model of thromboembolic stroke", Journal of Cerebral Blood Flow and Metabolism, 30(4): 718-728, 2010.
Eckert et al., "Liposome-incorporated DHA increases neuronal survival by enhancing non-amyloidogenic APP processing", Biochimica et Biophysica Acta, 1808: 236-243, 2011.
Extended European Search Report issued in European Application No. 13828100.1, dated Feb. 12, 2016.
Hoyte et al., "The rise and fall of NMDA antagonists for ischemic stroke", Current Molecular Medicine, 4: 127-132, 2004.
International Preliminary Report on Patentability issued in International Application No. PCT/US2013/054349, dated Feb. 10, 2015.
International Search Report and Written Opinion issued in International Application No. PCT/US2013/054349, dated Aug. 20, 2014.
International Search Report and Written Opinion issued in International Application No. PCT/US2014/030210, dated Oct. 17, 2014.
James, "Xenon Protects Against Brain Injury in Both Ischemic and Hemorrhagic Stroke", Am. Soc. Anaesthesiol., Conference Abstract, 2011.
Lee et al., "Memantine Reduces Hematoma Expansion in Experimental Intracerebral Hemorrhage, Resulting in Functional Improvement," journal of Cerebral Blood Flow & Metabolism (26) 536-544, 2006.
Office communication issued in Australian Application No. 2013299453, dated May 17, 2017.
Office Communication issued in Chinese Application No. 201210356929.9, dated Nov. 15, 2017.
Office Communication issued in Chinese Application No. 201210356929.9 dated Mar. 31, 2017.
Office Communication issued in Chinese Application No. 201210356929.9, dated Oct. 12, 2015.
Peng et al., "Abstract 3977: Neuroprotective effects of echogenic liposomes-mediated xenon delivery in a rat embolic stroke model combined with tissue plasminogen activator thrombolysis", International Stroke Conference Poster Abstracts, 43:A3977, 2012.
Shaw et al., "Ultrasound-enhanced thrombolysis with tPA-loaded echogenic liposomes", Thrombosis research, 124(3): 306-310, 2009.

* cited by examiner

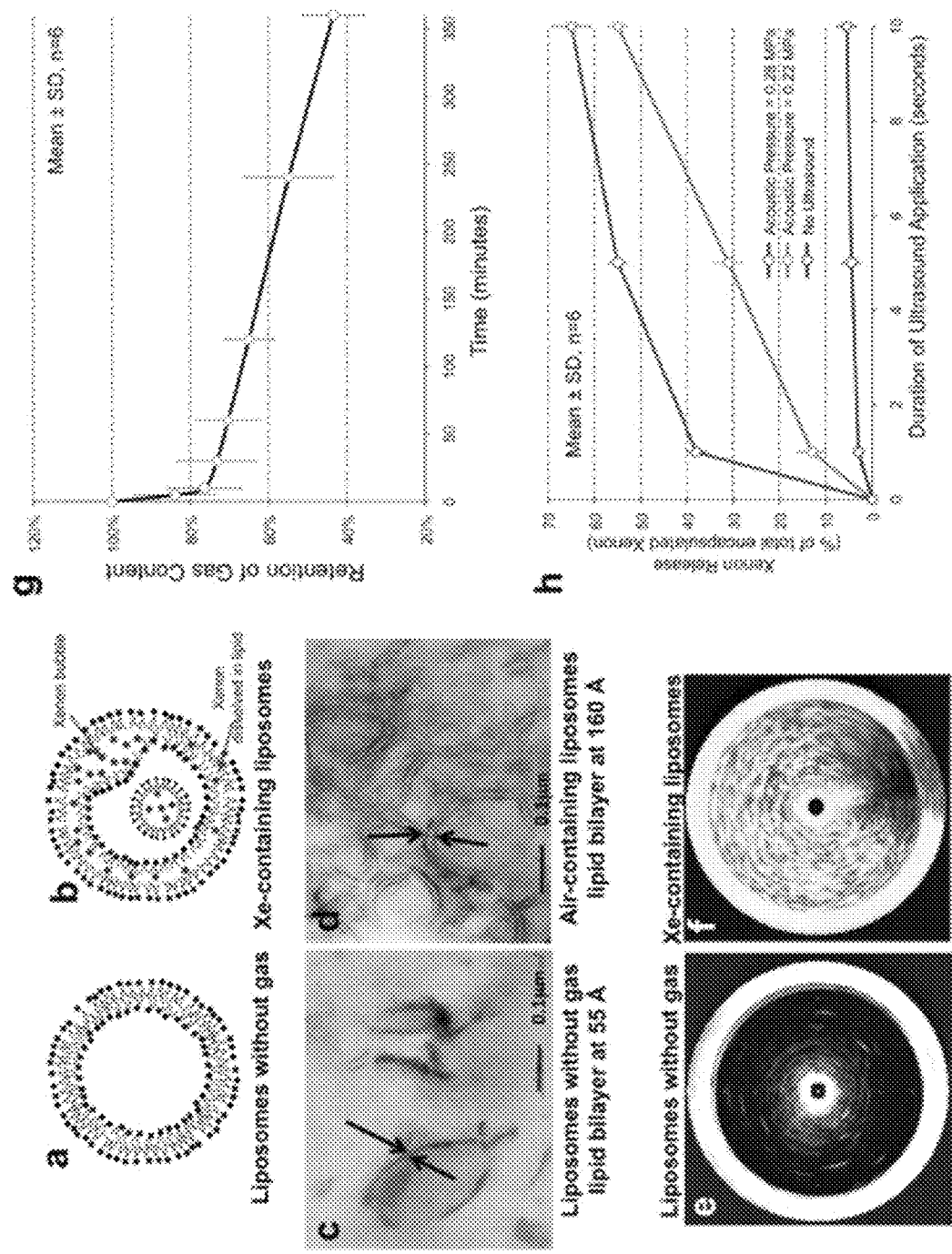
FIGS. 1a-h

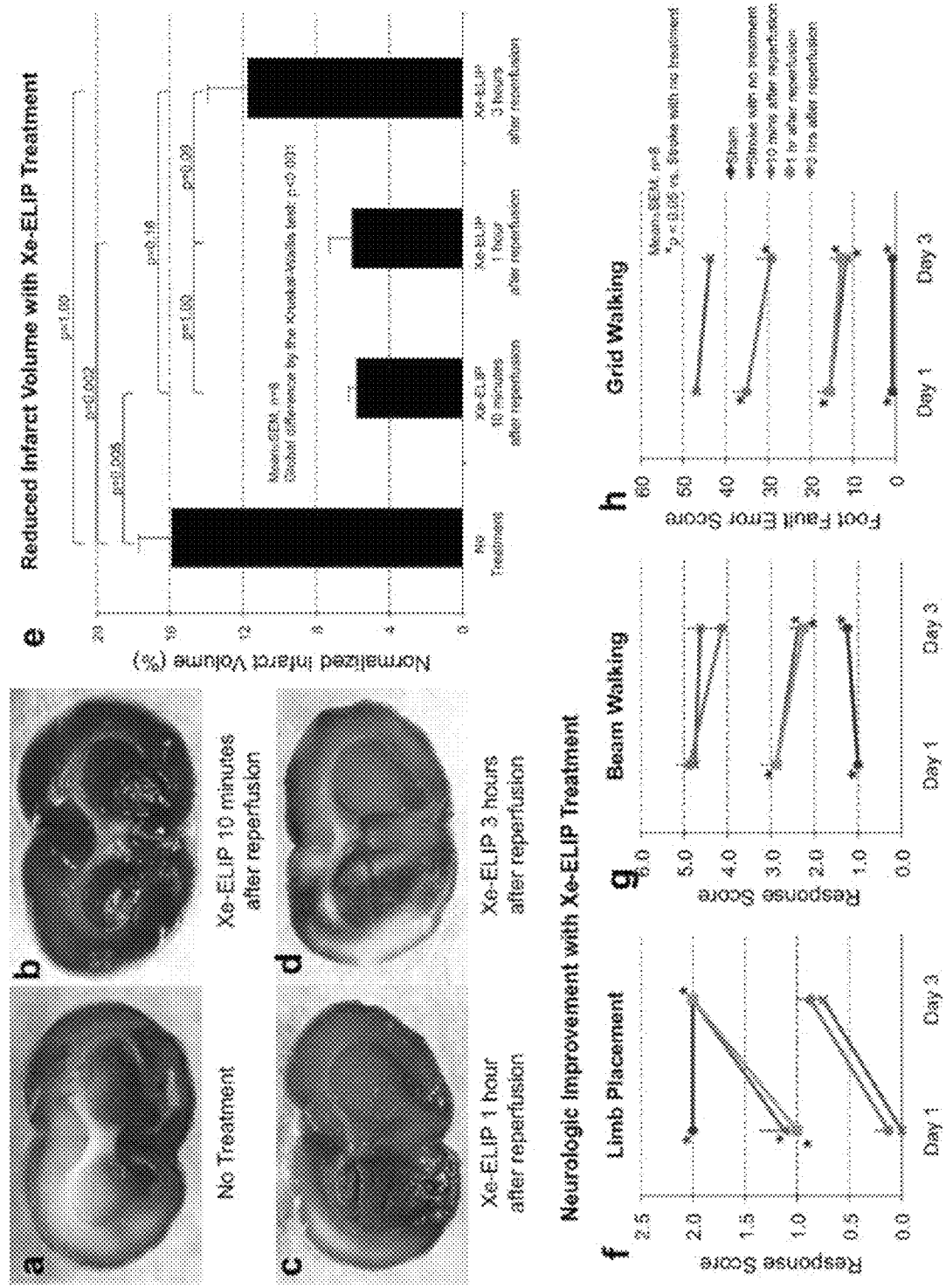
FIGS. 2a-h

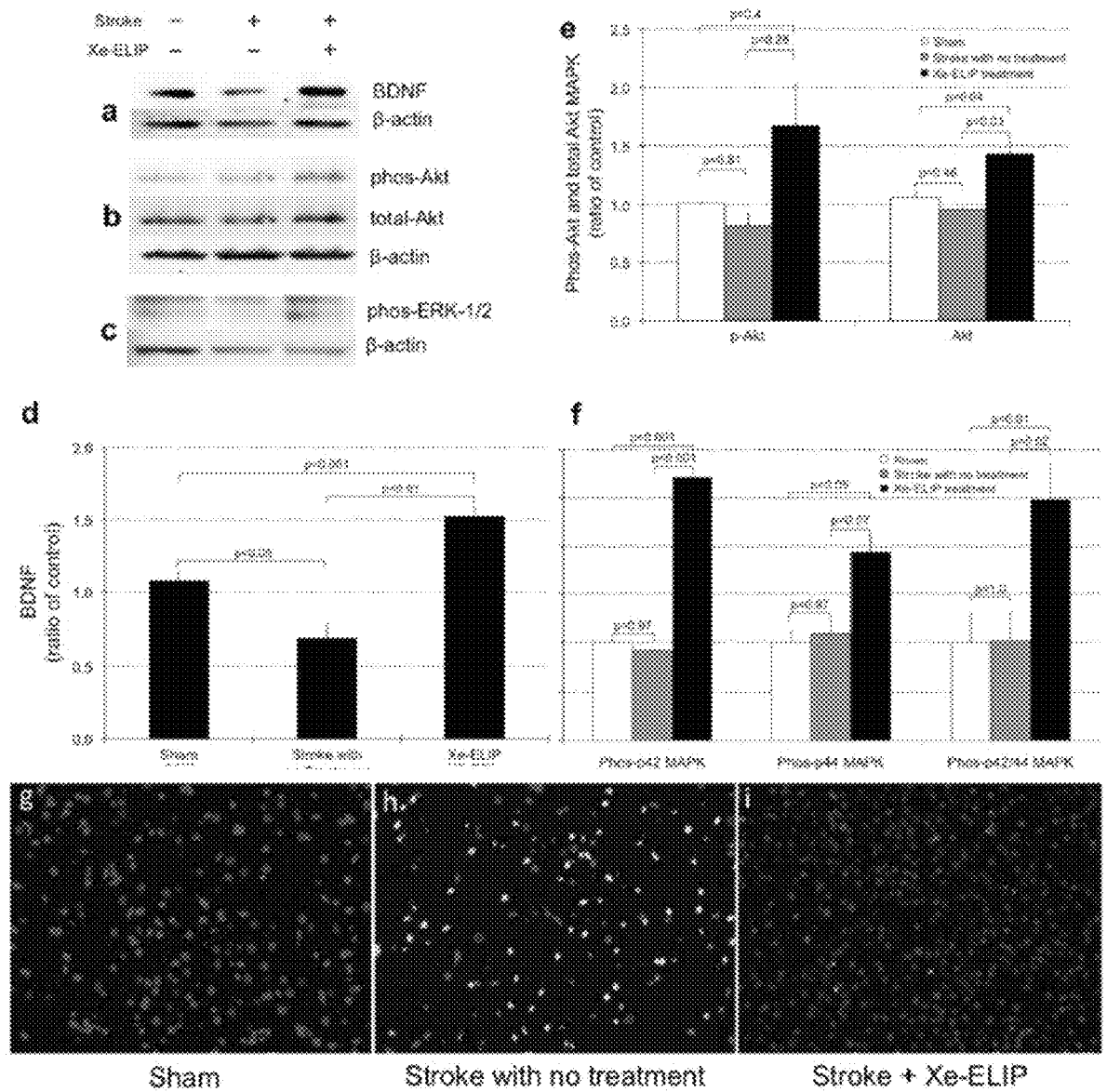
FIGS. 3a-i

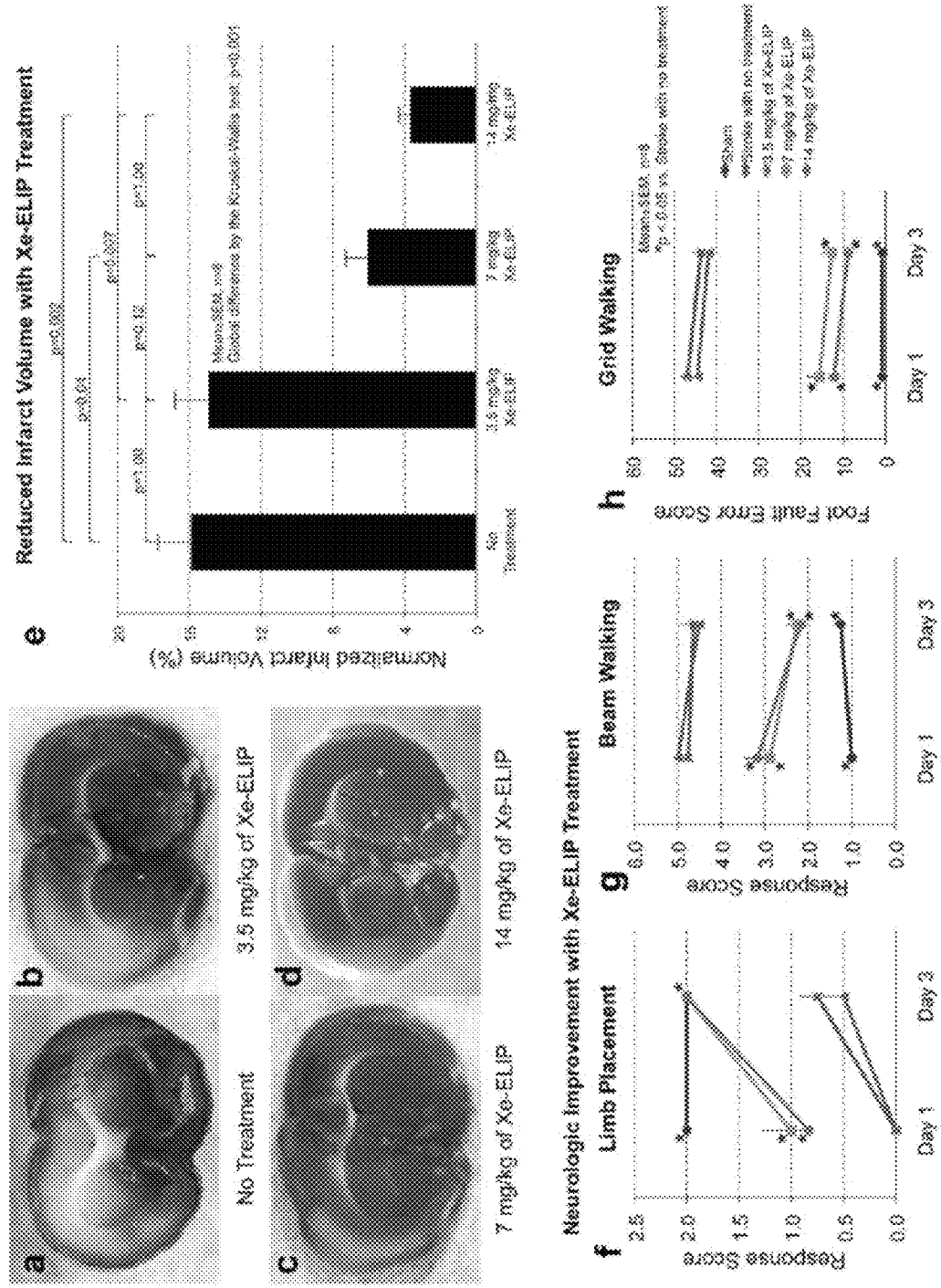
FIGS. 4a-h

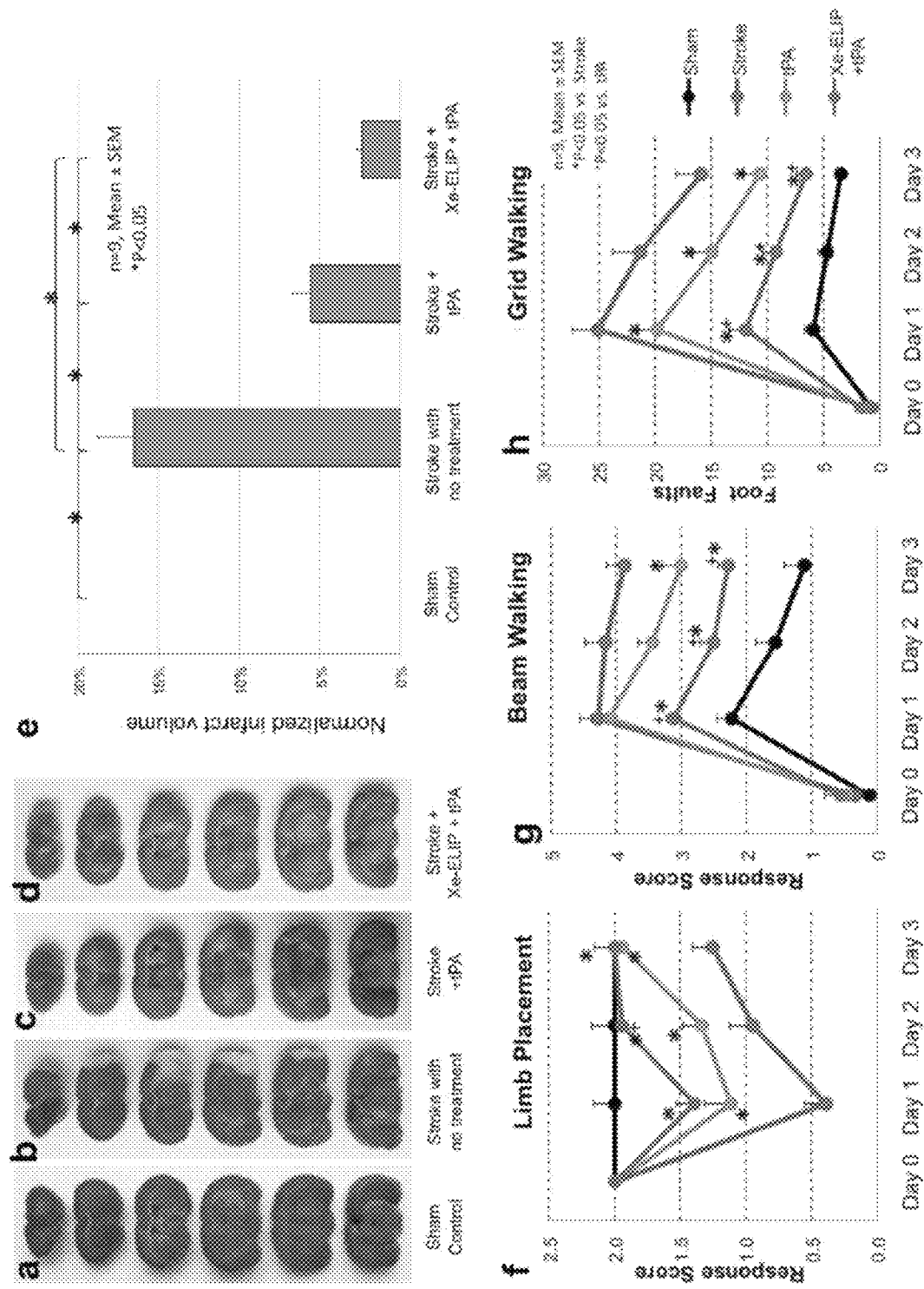
FIGS. 5a-h

FIGS. 13a-c

NEUROPROTECTIVE LIPOSOME COMPOSITIONS AND METHODS FOR TREATMENT OF STROKE

This application is a continuation of U.S. patent application Ser. No. 14/420,429, filed Feb. 9, 2015, which is a national phase application under 35 U.S.C. § 371 of International Application No. PCT/US2013/054349, filed Aug. 9, 2013, which claims the benefit of U.S. Provisional Patent Application No. 61/682,130, filed Aug. 10, 2012, the entire text of each which are incorporated herein by reference. This application also claims the benefit of Chinese Patent Application no. 201210356929.9, filed Sep. 21, 2012.

The invention was made with government support under Grant Nos. NS067454, HL 074002 and HL 059586 awarded by the National Institutes of Health. The government has certain rights in the invention.

BACKGROUND OF THE INVENTION

1. Field of the Invention

The present invention relates generally to the field of medicine, biochemistry and molecular biology. More particularly, it concerns compositions and methods of using biologically protective liposomes for the treatment of stroke.

2. Description of Related Art

Thrombotic and hemorrhagic strokes, also known as cerebrovascular accidents (CVA), are, together, the fourth leading cause of death in the United States and the most common cause of adult disabilities. Both types of stroke are characterized by a rapid loss of brain function due to disturbance in the blood supply to the brain. In thrombotic stroke, occlusion of a cerebral artery caused by a blood clot, results in brain tissue ischemia or obstruction of cerebral blood flow to a portion of the brain, and ultimately brain damage. Conversely, in hemorrhagic stroke, blood leaks or bursts from broken blood vessels inside or on the surface of the brain leading to neurological damage. Regardless of the type of stroke, early protection of brain tissues against the acute vascular events caused by thrombosis or hemorrhage by medical intervention remains the most crucial element to save patients' lives. The early brain tissue protection can broaden the safe window for differential diagnosis and effective treatment. Despite similar initial symptoms at onset, effective therapeutic intervention depends upon the type of stroke that a patient is experiencing. For example, administration of tissue plasminogen activator (tPA) has proven at least partially effective in treatment of thrombotic stroke, but is counter indicated for treatment of hemorrhagic stroke. There remains a need for new effective therapeutics for treatment of stroke, in particular, therapeutics that are amenable to immediate administration upon stroke onset.

SUMMARY OF THE INVENTION

In a first embodiment there is provided a method for treating a stroke in a subject comprising administering an effective amount of a composition comprising Xenon-loaded echogenic liposomes (Xe-ELIP) to the subject. In some aspects, the subject has been determined to have a hemorrhagic stroke. In a further embodiment, there is provided a method treating a stroke of undetermined origin in a subject (i.e., a subject not yet determined to have a thrombotic or hemorrhagic stroke) comprising administering an effective amount of a composition comprising Xe-ELIP to the subject. Thus, in some aspects, a method is provided for treating both hemorrhagic and thrombotic stroke in a subject (e.g., a subject that has been diagnosed with a hemorrhagic and/or thrombotic stroke). In still further aspects, a method of the embodiments is defined as a method of treating an intracranial aneurysm or subarachnoid hemorrhage in a subject comprising administering an effective amount of a composition comprising an effective amount of Xe-ELIP to the subject. In some embodiments there is provided a composition comprising Xe-ELIP in a pharmaceutically acceptable carrier.

In a further embodiment methods and compositions of the embodiments employ a different noble gas loaded in echogenic liposomes (in place of or in addition to Xenon). For example, in some aspects, echogenic liposomes for use according to the embodiments are loaded with Xenon, Helium, Argon, Krypton, Neon or a mixture thereof. Thus, in some aspects, there is provided a method for treating a stroke in a subject comprising administering an effective amount of a composition comprising Xenon, Helium, Argon, Krypton, or Neon-loaded echogenic liposomes to the subject. In further aspects, the subject has been determined to have a hemorrhagic stroke. In a further embodiment, there is provided a method treating a stroke of undetermined origin in a subject (i.e., a subject not yet determined to have a thrombotic or hemorrhagic stroke) comprising administering an effective amount of a composition comprising Xenon, Helium, Argon, Krypton, or Neon-loaded echogenic liposomes to the subject. Thus, in some aspects, a method is provided for treating both hemorrhagic and thrombotic stroke in a subject (e.g., a subject that has been diagnosed with a hemorrhagic and/or thrombotic stroke). In still further aspects, a method of the embodiments is defined as a method of treating an intracranial aneurysm or subarachnoid hemorrhage in a subject comprising administering an effective amount of a composition comprising an effective amount of Xenon, Helium, Argon, Krypton, or Neon-loaded echogenic liposomes to the subject. In some embodiments there is provided a composition comprising Xenon, Helium, Argon, Krypton, or Neon-loaded echogenic liposomes in a pharmaceutically acceptable carrier.

In a further embodiment there is provided a method of treating a thrombotic stroke in a subject comprising (a) administering an effective amount of a first composition comprising Xe-ELIP to the subject; and (b) administering an effective amount of a second composition comprising tissue plasminogen activator (tPA) to the subject. For example, in certain aspects, Xe-ELIP and tPA are administered sequentially or essentially simultaneously (e.g., in a composition comprising Xe-ELIP and tPA). In some aspects, a method of the embodiments comprises administering the second composition about or less than about 2, 3, 4, 5, 6, 7, or 8 hours after administration of the first composition. In still further aspects, administration of the first composition is within about 6 hours or less of stroke onset. In yet still further aspects, the second composition further comprises and effective amount of Xe-ELIP. In still a further aspect, a method of the embodiments comprises (a) administering an effective amount of a first composition comprising Xe-ELIP to a subject having a stroke or symptoms of a stroke of undetermined origin; (b) identifying whether the subject is suffering from a thrombotic or hemorrhagic stroke; and (c) administering an effective amount of a second composition comprising tPA to a subject identified as having a thrombotic stroke.

Thus, in further embodiment, there is provided a pharmaceutical composition comprising Xe-ELIP and tPA. In some aspects, the tPA of the composition is comprised in liposomes (e.g., echogenic liposomes). In further aspects, the composition comprises a slurry of at least two different liposome where the first liposomes are comprised of Xe-ELIP and the second liposomes comprise tPA (e.g., wherein tPA liposomes are essentially free of Xe).

In yet a further embodiment there is provided a pharmaceutical composition comprising noble gas-loaded-ELIP (e.g., Xe-ELIP) and liposomes (e.g., echogenic liposomes) loaded with a further biologically active gas component. For example, in some aspects noble gas-loaded echogenic liposomes may further comprise (or may be administered in conjunction with liposomes comprising) $H_2S$ and/or $H_2$. Likewise, in some aspects, noble gas-loaded echogenic liposomes may further comprise (or may be administered in conjunction with liposomes comprising) nitrous oxide and/or nitric oxide. For example, in some aspects, the gases are comprised in separate liposomes in the composition (e.g., a slurry of liposomes loaded with different gases). In further aspects, two or more of the gases are comprised in the same liposomes. For example, a composition can comprise liposomes that comprise Xe and NO, Xe and $N_2O$ or Xe, NO and $N_2O$. In another example, a composition can comprise liposomes that comprise Xe and $H_2$, Xe and $H_2S$ or Xe, $H_2$ and $H_2S$. In further aspects, liposomes of the embodiments comprise between about 0.1% and 5%, 0.1% and 3% or 0.5% and 2% $H_2S$ (as a percent of total gas in the liposome). For example, the liposomes can comprise about 1% $H_2S$ and about 99% Xe. In yet further aspects, liposomes of the embodiments comprise between about 1% and 50%, 5% and 40% or 10% and 40% $H_2$ (as a percent of total gas in the liposome). For example, the liposomes can comprise about 30% $H_2S$ and about 70% Xe.

Certain aspects of the embodiments concern compositions comprising tPA. In some aspects, the tPA is purified or recombinant mammalian tPA (e.g., human tPA). Such tPA compositions may be comprised in a pharmaceutically acceptable carrier. In certain aspects, the tPA is comprised in liposomes. Liposomes for use in encapsulating tPA can be selected from any other those known in art or detailed herein. For instance, in some aspects, the tPA is comprised in echogenic liposomes of the embodiments. In certain preferred aspects, liposomes comprising tPA are essentially free of Xe (i.e., tPA and Xe are not loaded into the same liposome vesicle).

Compositions in accordance with the embodiments can be administered to a subject via an array of methods. For example, in some aspects, compositions (e.g., Xe- or tPA-containing compositions) are administered intravenously, intra-arterially, intracranially, via intravenous infusion or via intra-arterial infusion. In preferred aspects, compositions of the embodiments are administered shortly after the onset of a stroke or stroke symptoms, such as about or less than about 1, 2, 3, 4, 5, 6 or 8 hours of stroke onset or the onset of stroke symptoms. Thus, in some aspects, compositions of the embodiments are administered by a first responder (e.g., a nurse or medical technician).

In certain aspects, a method of the embodiments comprises administering one or more doses of an ELIP composition (e.g., a Xe-ELIP composition) to a subject. For example, in some aspects, a subject is administered a dose of between about 0.6 and 3.0 mg/kg of Xe-ELIP, such as a dose of between about 0.8 and 2.8 mg/kg (mg-lipid/kg-subject). In further aspects, a subject is administered a dose of between about 1.0 and 2.5 mg/kg of an ELIP composition, such as about 1.14 mg/kg or about 2.27 mg/kg. In still further aspects, ELIP compositions are provided that comprise a single unit dosage (e.g., of Xe-ELIP) in a suitable containment means. For example, the single unit dosage (i.e., a dose suitable for a human subject of about 60 kg) can be about 100 to about 3,000 mg; about 250 to about 2,000 mg; about 250 to about 1,000 mg; or about 400 to about 900 mg (e.g., 480-900 mg) of ELIP with an encapsulated gas (based on total lipid weight). In still further aspects, a single unit dosage of Xe-ELIP can be defined by the total volume of encapsulated Xe. In some aspects, the total volume of Xe in a single dose is less than about 5 ml, such as between about 0.1 and 2.5 ml; about 0.2 and 2.0 ml; or 0.5 and 1.5 ml (e.g., a dose of about 1.0 ml) of Xe. Thus, in some specific aspects, a single unit dosage of Xe-ELIP is provided comprising between 250 to about 1,000 mg of lipid and between about 0.1 and 2.5 ml of Xe in suitable containment means. A skilled artisan will recognize that any of the forgoing dose ranges may also be applied to Xe-ELIP compositions that include $H_2$ and/or $H_2S$ (in this case gas volumes can be applied to the total amount of encapsulated gas).

In still a further aspect, a composition (e.g., an ELIP composition) of the embodiments is administered to a subject in multiple doses. For example, in some aspects, the composition is administered to the subject a second, third or fourth time. In certain aspects, the formulation, dosage or route of the second dosage or subsequent administration can be adjusted relative to the first administration. In some aspects, the second or subsequent administration is about or less than about 2, 3, 4, 5, 6, 7, or 8 hours after the initial administration (e.g., within about 4-6 hours after the first administration). In some aspects, a composition of the embodiments is administered to a subject twice within about 12 hours of the onset of a stroke or stroke symptoms.

In preferred aspects a subject for treatment in accordance with the embodiments is a human in subject. However, in some aspects, the subject can be a non-human animal, such a non-human primate or a domesticated animal such a horse, dog or cat. In further aspects, the subject is identified as having symptoms of stroke, such as sudden memory loss, full or partial paralysis, disorientation, trouble speaking, sudden vision impairment, numbness of a portion of the body, sudden, severe, headache or trouble walking or balancing. In some aspects, the subject having a stroke or stroke symptoms has not been identified as having a thrombotic stroke or a hemorrhagic stroke. In still further aspects, the subject has been identified as having a thrombotic stroke and/or a hemorrhagic stroke.

In further aspects, administration of an ELIP composition of the embodiments to a subject further comprises applying ultrasound stimulation to the subject in an amount effective to promote gas release from the liposomes. For example, the ultrasound stimulation can be applied after or concomitantly with administration of the ELIP composition. In some aspects, the ultrasound stimulation is applied after the administration of an ELIP composition (e.g., Xe-ELIP) such as about or less than about 10 seconds, 20, seconds, 30 seconds or 1, 2, 3, 4 or 5 minutes after the administration. In certain cases the ultrasound stimulation is applied at or near the site of desired gas release by the liposomes. For example, in the case of a subject having a stroke, ultrasound stimulation can be applied to the head or neck (e.g., at the carotid artery) thereby stimulating release of liposomal payload proximal to the brain.

A variety of methods for applying ultrasound stimulation to a subject are known and can be used in accordance with the embodiments. For example, the ultrasound stimulation can be applied with a conventional ultrasound probe or a cervical collar ultrasound device (e.g., to provide stimulation at the neck). The power and frequency of ultrasound stimulation applied to a subject can vary, but generally will be an amount effective to promote Xe release (e.g., in vivo release) from liposomes. For example, the ultrasound stimulation can be applied at a frequency of between about 1 and 8 MHz, with a mechanical index of between about 0.1 and 1.4.

In still further aspects a method of the embodiments further comprises administering at least a second therapeutic agent to the subject. For example, in the case of thrombotic stroke the second therapeutic can be a blood clot reducing thrombolytic agent. In further aspects, the second therapeutic agent is an anti-inflammatory agent or a neuroprotective agent. In some specific aspects, e.g., in the case of thrombotic stroke, tPA is administered to a subject.

In certain specific aspects, the second therapeutic agent comprises $H_2S$ and/or $H_2$-loaded echogenic liposomes. In some cases, the $H_2S$ and/or $H_2$-loaded echogenic liposomes and the Xe-loaded echogenic liposomes are comprised in the same composition. For example, a composition of the embodiments can comprise echogenic liposomes that, separately, comprise Xe, $H_2S$ and/or $H_2$. Alternatively, the compositions can comprise echogenic liposomes that comprise two or three gases (e.g., two or more gases selected from Xe, $H_2S$ and $H_2$).

In still further aspects, a method of administration in accordance with the embodiments comprises preparing a liquid liposome suspension prior to administration to a subject. For example, in some aspects, the liquid liposome suspension is prepared no more than 30 minutes, 10 minutes, 5 minutes or 2 minutes prior to administration. For example, in some aspects, preparing a liquid liposome suspension comprises suspending lyophilized liposomes in a solution or thawing a frozen liposome suspension.

In further aspects an ELIP composition of the embodiments comprises additional components, such as preservatives, stabilizers and/or salts. In some aspects, ELIP compositions comprise at least a first cryoprotectant. Cryoprotectants for use according to the embodiments include, without limitation, mannitol, glycerol, trehalose, 1,2-propanediol or dimethylsulfoxide (DMSO).

As used herein an echogenic liposome refers to a liposome that can be imaged by ultrasound. In particular aspects, an echogenic liposome is a liposome that comprises a gas component (e.g., Xe, $H_2S$ and/or $H_2$), such as gas comprised in the hydrophobic layer of the liposome. Echogenic liposome compositions and methods for making such composition are provided for example is U.S. Pat. Nos. 5,612,057; 5,858,399; and 7,976,743, each of which is incorporated herein by reference. In some aspects, liposomes of the embodiments (e.g., ELIP compositions) are defined by the average particle size. For example, in some aspects the liposomes have an average size of about 0.4 to 10 microns or 0.8 to 10 microns (e.g., an average size of about 0.4, 0.5, 0.6, 0.7, 0.8, 0.9, 1.0, 2.0, 3.0, 4.0, 5.0, 6.0, 7.0, 8.0, 9.0 or 10.0 microns).

A wide array of components can be used to formulate a liposome of the embodiments, such as ELIP loaded with a gas such as Xe, $H_2$ and/or $H_2S$. For example, a liposome of the embodiments can comprise any form of phosphatidylcholine (PC) (such as dipalmitoyl phosphatidylcholine (DPPC)), any form of phosphoethanolamine (PE), a polyethylene glycol (PEG) or a PEGylated phospholipid, any form of phosphatidylglycerol (PG) (such as 1,2-dipalmitoyl-sn-glycero-3-phospho-(1'-rac-glycerol) (DPPG)) and/or cholesterol. In some aspects, a liposome comprises at least one PC, PE, negatively-charged lipid, PEGylated lipid (e.g., PEG2000-DPPE) and cholesterol molecule. In some specific aspects, a liposome comprises DPPC, Egg PC (EPC), PEG2000-DPPE, DPPG and cholesterol. In still further aspects a liposome of the embodiments consists of or consists essentially of DPPC, EPC, PEG2000-DPPE, DPPG, cholesterol and Xenon. In still further aspects, a liposome consists of or consists essentially of DPPC, EPC, PEG2000-DPPE, DPPG, cholesterol, Xe and $H_2$, $H_2S$ or a combination of $H_2$ and $H_2S$.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1a-h: Characterization of xenon-containing liposome and ultrasound-triggered xenon release. (a) Traditional liposome without gas. (b) Liposome containing Xe, made by the pressurized-freezing method, with Xe entrapped in the lipid bilayer as a dissolved gas or a bubble. (c and d) Electron microscopic image of traditional liposome and gas-containing liposome showed a wide lipid bilayer for gas-containing liposomes. Intravascular ultrasound imaging of traditional liposome (e) and Xe-containing liposome (f) showed a high ultrasound reflectivity from Xe-containing liposomes. (g) Ultrasound release of xenon from Xe-ELIP has two phases: a fast release in first 30 min followed by a slow release lasting more than 18 h (half-life 4.97±0.7 hours). Ultrasound triggered the release of Xe from Xe-ELIP in a power-dependent manner (h).

FIGS. 2a-h: Time window of Xe-ELIP's neuroprotective effect. Coronal brain sections (TTC staining) of middle cerebral artery occlusions without treatment (a) and with Xe-ELIP (7 mg/kg) treatment at 10 min (b), 1 h (c) and 3 h (d) after reperfusion. The white areas are the infarcted regions after middle cerebral artery occlusion; (e) Quantification of the infarct volume of the brain showed that Xe-ELIP administration at 10 min and 1 h after reperfusion was significantly different from the no treatment group. Neurological assessments of limb placement (f), beam walking (g), and grid walking (h) showed similar results as the TTC staining. Data are means±standard error.

FIGS. 3a-i: Effects of Xe-ELIP on BDNF expression and apoptosis. Western blot analysis of BDNF (a), phos-Akt (b) and phos-ERK (c) in cerebral cortex tissue 24 h after stroke showed that Xe increased the expression of BDNF (d), total Akt (e) and phos-ERK (f). TUNEL staining in the penumbral region of brain sections from the sham-operated group (g), stroke group (h) and stroke with Xe-ELIP treatment group (i) showed reduction of apoptosis in Xe-ELIP-treated animals. The Western blots and photomicrographs of apoptosis are representative of three independent experiments. Data are means±SD.

FIGS. 4a-h: Dose response of Xe-ELIP's neuroprotective effect. Coronal brain sections (stained with TTC) of middle cerebral artery occlusions were imaged without treatment (a), and with 3.5 mg/kg (b), 7 mg/kg (c) and 14 mg/kg (d) of Xe-ELIP. The white areas are the infarcted regions after middle cerebral artery occlusion. Quantification of the infarct volume of the brain is shown in (e). Neurological assessments of limb placement (f), beam walking (g), and grid walking (h) are provided in the indicated graphs. Data are means±standard error.

FIGS. 5a-h: Effects of IV tPA in combination with Xe delivery on cerebral ischemia. Representative TTC-stained coronal brain sections showing brain infarction in rats 3 days after middle cerebral artery occlusion were imaged after (a) sham, (b) ischemic stroke without treatment, (c) ischemic stroke with tPA treatment (d) ischemia stroke with Xe-ELIP in combination with tPA. (e) A comparison of infarct sizes between treatment groups showing a 69% reduction in infarct volume with tPA alone and a 75% reduction with Xe-ELIP combined with IV tPA. Neurological assessments of limb placement (f), beam walking (g) and grid walking (h) are shown in the indicated graphs. Data are means±standard error.

DESCRIPTION OF ILLUSTRATIVE EMBODIMENTS

I. The Present Invention

Stroke also known as cerebrovascular accident (CVA), is the third leading cause of death in the United States and the most common cause of adult disabilities. A stroke is characterized by a rapid loss of brain function due to disturbance in the blood supply to the brain. In thrombotic stroke, occlusion (a blood clot) of a cerebral artery, resulting in obstructed blood flow to a portion of the brain. Conversely, in hemorrhagic stroke blood leaks or bursts from blood vessels in the brain leading to neurological damage. Early therapeutic and/or surgical intervention is crucial in mitigating neurological damage from stroke. However, depending upon the type of stroke the therapy administered is quite different, to the extent that therapeutics, such as tPA, cannot be administered to a patent having a stroke unless the type of stroke has been positively identified. Unfortunately, the most crucial factor in treatment of stroke is timely intervention, which limits the usefulness of therapeutics such as tPA.

Studies detailed here demonstrate the synthesis of a new kind of echogenic liposome that encapsulates Xenon gas (Xe-ELIP). The Xe-ELIP formulations are demonstrated to quickly and effectively release encapsulated Xe upon application of ultrasound (FIG. 1). Compositions comprising these liposomes are also shown to be effective not only in the treatment of thrombotic stroke, but also surprisingly, for treatment of hemorrhagic stroke (see FIGS. 2, 4, 8, and 9). Thus, for the first time, Xe-ELIP represents a therapeutic that can be administered to a patient immediately following a stroke (or the onset of stroke symptoms) and before the type of stroke can be positively identified. Unlike any other identified therapy Xe-ELIP thus, can protect neurons from the insults that result from both blood clot (ischemia) and hemorrhage. Importantly, Xe-ELIP buys the patient crucial time by protecting the brain from excessive neurological damage (as assessed both by actual neuronal damage and behavioral testing) while surgical or other therapeutic interventions can be implemented. Accordingly, this new class of therapeutic offers the possibility of significantly improving clinical outcome of all classes of stroke.

Interestingly, studies detailed herein likewise demonstrate that Xe-ELIP can work in concert with tPA administration in providing effective treatment for thrombotic stroke (see, FIG. 5). Here again, early treatment with Xe-ELIP prevents excessive neuronal damage while the stroke diagnosis is assessed. Subsequent administration of tPA (with or without additional Xe-ELIP) then mediates clot break-down, resulting in significantly better clinical outcome as compared to tPA alone.

Figure 13:
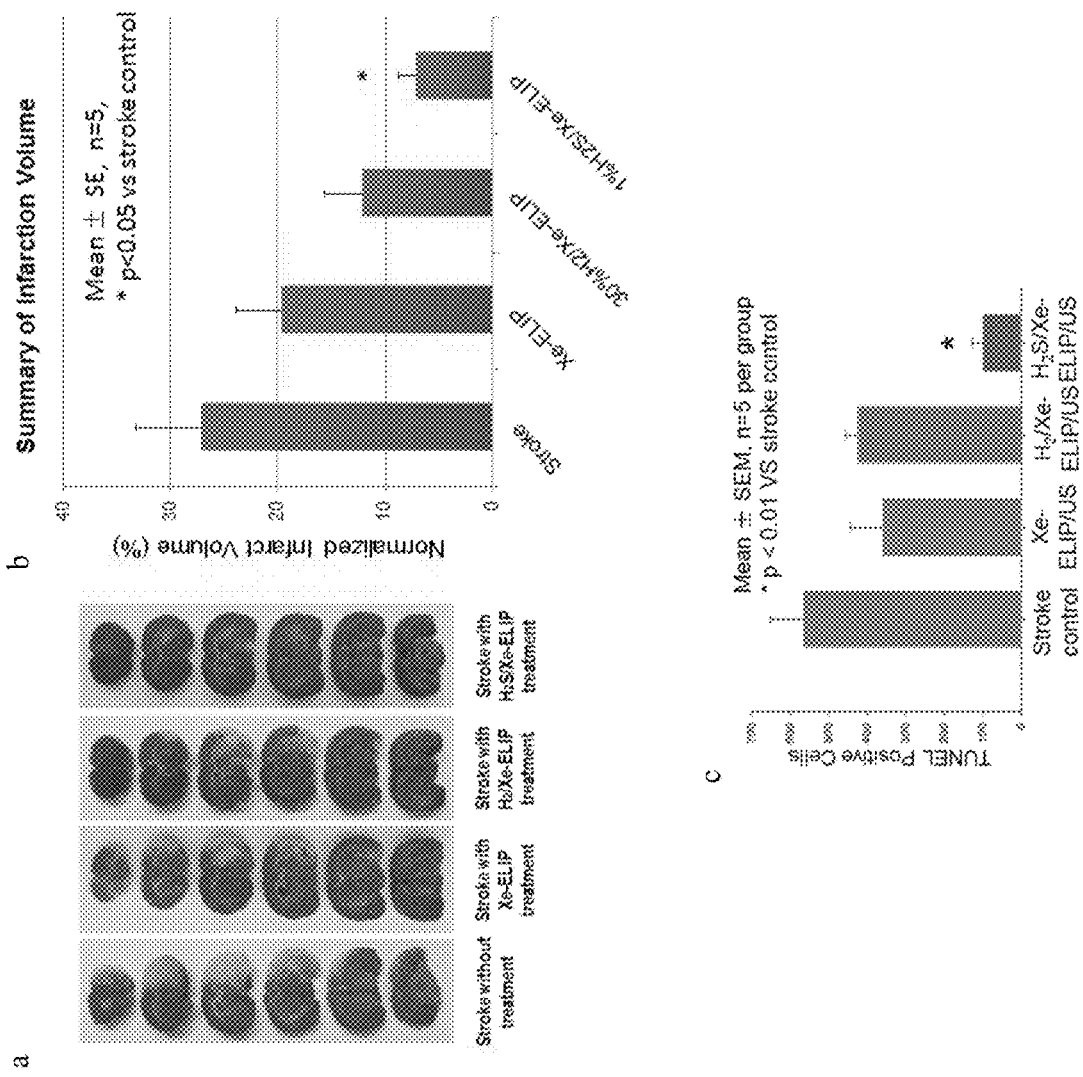
FIGS. 13a-c: Results of stroke treatment with Xe-ELIP, H$_2$S/Xe-ELIP and H$_2$/Xe-ELIP in the tMCAO model are shown. (a) Representative TTC-stained coronal brain sections showing brain infarction. (b) A summary comparison of infarct volumes between treatment groups. (c) Graphical representation of TUNEL staining of brain sections from each treatment group.
Figure 14:
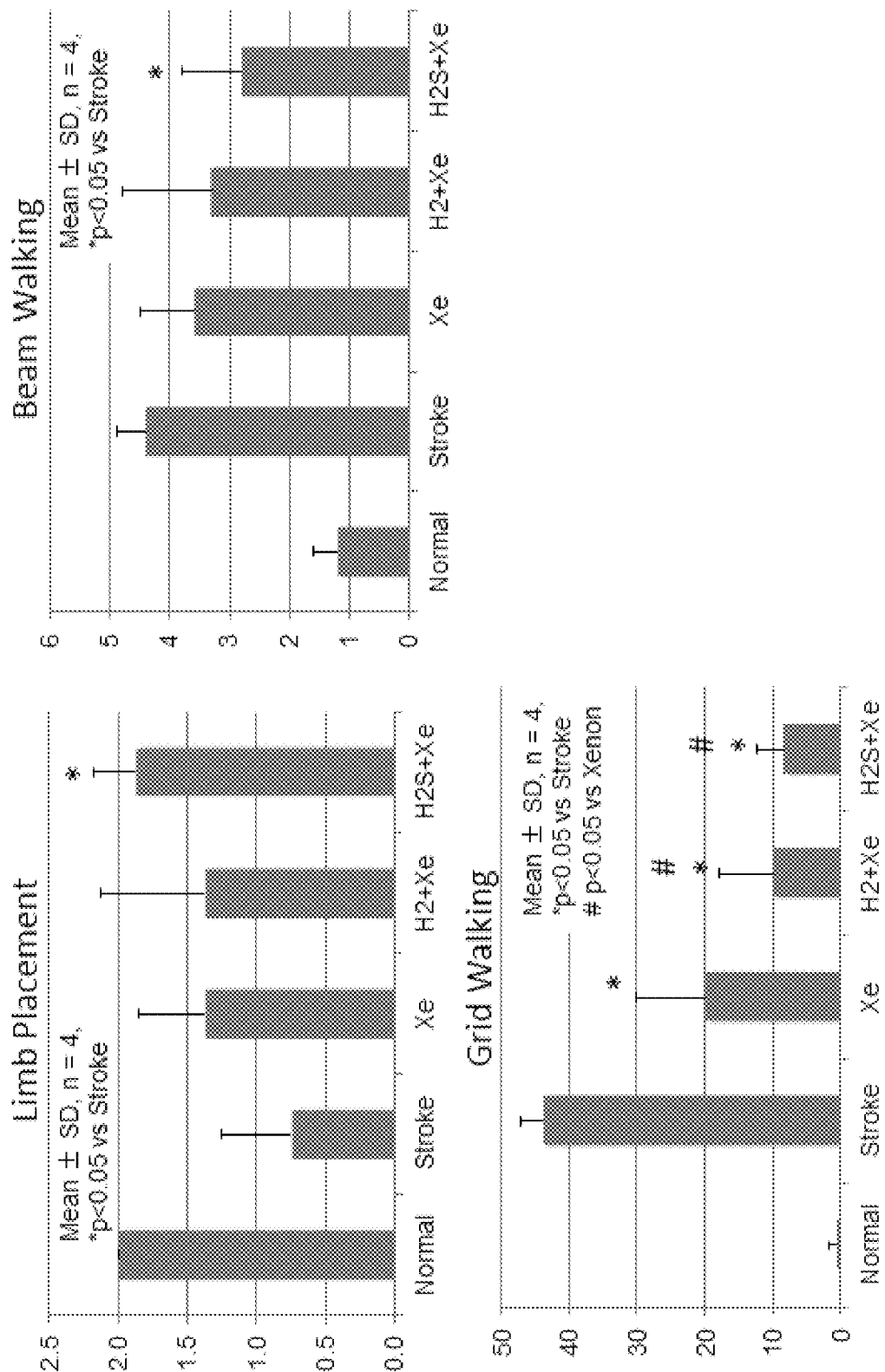
FIG. 14: Graphs show the results of behavioral tests for neurologic disability in rats treated with the indicated composition as assessed by limb placement, beam walking and grid walking, as indicated.

Further studies presented herein demonstrate the neuroprotective effect of Xe-ELIP can be yet further enhanced by co-administration (or administration of co-encapsulated) $H_2$ or $H_2S$ gas. As shown in FIGS. 13-14 both $H_2$ and $H_2S$, when administered in conjunction with Xe-ELIP, are able to further reduce infarct volume and further improve outcome in stoke subjects as assessed by behavioral testing. Furthermore, as demonstrated in FIG. 16 none of the ELIP compositions (comprising Xe or Xe and $H_2$ or $H_2S$) showed significant toxicity as assessed in murine embryonic stem cells. Accordingly, the further incorporation of $H_2$ and/or $H_2S$ into Xe-ELIP compositions may yet further enhance their neuroprotective efficacy.

II. Liposomes and Liposome Compositions

A "liposome" is a generic term encompassing a variety of single and multilamellar lipid vehicles formed by the generation of enclosed lipid bilayers or aggregates. Liposomes may be characterized as having vesicular structures with a bilayer membrane, generally comprising a phospholipid, and an inner medium that generally comprises an aqueous composition. Liposomes provided herein include unilamellar liposomes, multilamellar liposomes and multivesicular liposomes. Liposomes provided herein may be composed of positively charged, negatively charged or neutral phospholipidsl. In certain embodiments, the liposomes are neutral in charge.

A multilamellar liposome has multiple lipid layers separated by aqueous medium. They form spontaneously when lipids comprising phospholipids are suspended in an excess of aqueous solution. The lipid components undergo self-rearrangement before the formation of closed structures and entrap water and dissolved solutes between the lipid bilayers (Ghosh and Bachhawat, 1991). Lipophilic molecules or molecules with lipophilic regions may also dissolve in or associate with the lipid bilayer.

In specific aspects, a gas is capsulated in a liposome to generate an echogenic liposome that can be imaged and/or disrupted by the appropriate application of ultrasound. Specific methods for gas encapsulation are detailed below and exemplified in Example 1 and FIGS. 1 and 7.

A liposome used according to the present embodiments can be made by different methods, as would be known to one of ordinary skill in the art. For example, a phospholipid (Avanti Polar Lipids, Alabaster, Ala.), such as for example the neutral phospholipid dioleoylphosphatidylcholine (DOPC), Dipalmitoyl Phosphatidylcholine (DPPC) and/or EPC, can be dissolved in an alcohol or other organic solvent and then mixed with a component for inclusion in the lipid bilayer. The mixture may further include various detergents. Typically, a lipid mixture is vortexed, frozen in a dry ice/acetone bath and lyophilized overnight. The lyophilized preparation is stored at −20° C. or less for extended periods of time. When required the lyophilized liposomes are reconstituted, for example, in 0.9% saline.

Alternatively, a liposome can be prepared by mixing lipids in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

In other alternative methods, liposomes can be prepared in accordance with other known laboratory procedures (e.g., see Bangham et al., 1965; Gregoriadis, 1979; Deamer and Uster, 1983; Szoka and Papahadjopoulos, 1978, each incorporated herein by reference in relevant part). Additional liposomes which may be useful with the present embodiments include cationic liposomes, for example, as described in WO02/100435A1, U.S. Pat. No. 5,962,016, U.S. Application 2004/0208921, WO03/015757A1, WO04029213A2, U.S. Pat. Nos. 5,030,453, and 6,680,068, all of which are hereby incorporated by reference in their entirety without disclaimer. A process of making liposomes is also described in WO04/002453A1. Neutral lipids can be incorporated into cationic liposomes (e.g., Farhood et al., 1995). Various neutral liposomes which may be used in certain embodiments are disclosed in U.S. Pat. No. 5,855,911, which is incorporated herein by reference. These methods differ in their respective abilities to entrap aqueous material and their respective aqueous space-to-lipid ratios.

The size of a liposome varies depending on the method of synthesis. Liposomes in the present embodiments can be a variety of sizes. In certain embodiments, the liposomes are small, e.g., less than about 100 nm, about 90 nm, about 80 nm, about 70 nm, about 60 nm, or less than about 50 nm in external diameter.

In preparing such liposomes, any protocol described herein, or as would be known to one of ordinary skill in the art may be used. Additional non-limiting examples of preparing liposomes are described in U.S. Pat. Nos. 4,728,578, 4,728,575, 4,737,323, 4,533,254, 4,162,282, 4,310,505, and 4,921,706; International Applications PCT/US85/01161 and PCT/US89/05040; U.K. Patent Application GB 2193095 A; Mayer et al., 1986; Hope et al., 1985; Mayhew et al. 1987; Mayhew et al., 1984; Cheng et al., 1987; and Liposome Technology, 1984, each incorporated herein by reference).

In certain embodiments, the lipid based nanoparticle is a neutral liposome (e.g., a DOPC liposome). "Neutral liposomes" or "non-charged liposomes", as used herein, are defined as liposomes having one or more lipid components that yield an essentially-neutral, net charge (substantially non-charged). By "essentially neutral" or "essentially non-charged", it is meant that few, if any, lipid components within a given population (e.g., a population of liposomes) include a charge that is not canceled by an opposite charge of another component (i.e., fewer than 10% of components include a non-canceled charge, more preferably fewer than 5%, and most preferably fewer than 1%). In certain embodiments, neutral liposomes may include mostly lipids and/or phospholipids that are themselves neutral under physiological conditions (i.e., at about pH 7).

Liposomes and/or lipid-based nanoparticles of the present embodiments may comprise a phospholipid. In certain embodiments, a single kind of phospholipid may be used in the creation of liposomes (e.g., a phospholipid, such as DPPC (composed of all saturated phosphatidylglycerol or phosphatidylserine), may be used to generate a liposome). In other embodiments, more than one kind of phospholipid may be used to create liposomes (e.g., DPPC and EPC).

Phospholipids include, for example, phosphatidylcholines, phosphatidylglycerols, and phosphatidylethanolamines; because phosphatidylethanolamines and phosphatidyl cholines are non-charged under physiological conditions (i.e., at about pH 7), these compounds may be particularly useful for generating neutral liposomes. In certain embodiments, the phospholipid DOPC is used to produce non-charged liposomes. In certain embodiments, a lipid that is not a phospholipid (e.g., a cholesterol) may be used Phospholipids include glycerophospholipids and certain sphingolipids. Phospholipids include, but are not limited to, dioleoylphosphatidylycholine ("DOPC"), egg phosphatidylcholine ("EPC"), dilauryloylphosphatidylcholine ("DLPC"), dimyristoylphosphatidylcholine ("DMPC"), dipalmitoylphosphatidylcholine ("DPPC"), distearoylphosphatidylcholine ("DSPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dilauryloylphosphatidylglycerol ("DLPG"), dimyristoylphosphatidylglycerol ("DMPG"), dipalmitoylphosphatidylglycerol ("DPPG"), distearoylphosphatidylglycerol ("DSPG"), distearoyl sphingomyelin ("DSSP"), distearoylphophatidylethanolamine ("DSPE"), dioleoylphosphatidylglycerol ("DOPG"), dimyristoyl phosphatidic acid ("DMPA"), dipalmitoyl phosphatidic acid ("DPPA"), dimyristoyl phosphatidylethanolamine ("DMPE"), dipalmitoyl phosphatidylethanolamine ("DPPE"), dimyristoyl phosphatidylserine ("DMPS"), dipalmitoyl phosphatidylserine ("DPPS"), brain phosphatidylserine ("BPS"), brain sphingomyelin ("BSP"), dipalmitoyl sphingomyelin ("DPSP"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl-sn-glycero-3-phosphocholine ("DEPC"), dioleoylphosphatidylethanolamine ("DOPE"), palmitoyloeoyl phosphatidylcholine ("POPC"), palmitoyloeoyl phosphatidylethanolamine ("POPE"), lysophosphatidylcholine, lysophosphatidylethanolamine, and dilinoleoylphosphatidylcholine.

Phospholipids may be from natural or synthetic sources. Phospholipids from natural sources, such as egg or soybean phosphatidylcholine, brain phosphatidic acid, brain or plant phosphatidylinositol, heart cardiolipin and plant or bacterial phosphatidylethanolamine (or hydrogenated versions thereof) are used, in certain embodiments, as the phosphatide. In some aspects, PEGylated lipids are employed such as PEG2000-DPPE=1,2-dipalmitoyl-sn-glycero-3-phosphoethanolamine-N-[methoxy(polyethylene glycol)-2000] (which could be all mPEG mPEG Phospholipids or all Phosphatidylethanolamine).

It will likewise be understood by a skilled worker that the molar ratios of various liposome components may be adjusted to optimize delivery, encapsulation, etc. In some aspects, for example, a liposome comprises DPPC:EPC:PEG2000-DPPE:DPPG:CH in a ratio of about 30-50:10-30:5-15:5-15:10-20, or about 40-50:20-30:5-10:5-10:10-20. Some examples of specific ratios include, without limitation, 50:20:10:10:15; 60:30:10:10:12; 46:23:8:8:15; 47:27:9:8:13; or 48:28:7:7:13.

In certain embodiments, the lipid-based vesicle is a DOTAP:cholesterol nanoparticle. DOTAP:cholesterol nanoparticles are prepared by mixing the cationic lipid DOTAP (1,2-bis(oleoyloxy)-3-(trimethylammonio)-propane) with cholesterol. Vesicles can further be prepared with a nucleic acid and can form a structure (called a "sandwich') where the nucleic acid appears to be condensed between two lipid bilayers (U.S. Pat. Nos. 6,770,291 and 6,413,544).

A. Gas-Loaded Liposomes

The present invention, in certain embodiments, provides methods for the facile production of gas-containing liposomes with simultaneous drug encapsulation. In exemplary embodiments (see Example 1), liposomes of phospholipid and cholesterol were prepared by conventional procedures of hydrating the lipid film, sonicating, freezing and thawing. The lipids generated contain air by including a step after sonication where the lipid is placed under pressure with the gas of interest. After equilibration, the sample is frozen. The pressure is then reduced to atmospheric and the suspension thawed. This procedure leads to entrapment of air in amounts up to about 10% by volume by lipid dispersions at moderate (10 mg/ml) concentrations. The amount of gas encapsulated increases with gas pressure and lipid concentration. Utilizing 0.32 M mannitol to provide an aqueous phase with physiological osmolarity, 1, 2, 4 or 6 atm of pressure was applied to 4 mg of lipid. This would led to encapsulation of 10, 15, 20, and 30 µl of gas, respectively. While the present embodiments are not limited to any particular mechanism, the mechanism for gas encapsulation presumably depends upon the fact that air (predominantly nitrogen and oxygen), like most solutes, dissolves poorly in ice and is excluded from the ice that forms during freezing. The excluded air then comes out of solution as air pockets that are stabilized in some form by a lipid coating. The presence of air in these preparations sensitizes them to ultrasound such that up to half of their aqueous contents (which could include a water soluble drug) can be released by short (e.g., 10 second) applications of ultrasound.

The present invention provides methods to introduce gas into liposomes such that they not only reflect ultrasound, but also release their contents when exposed to ultrasound or other triggering procedure. Of practical importance is that the method, which, in certain embodiments, uses elevated-pressure in combination with freezing, is very simple and allows ready encapsulation of solutes along with incorporation of a gas of choice. The method is suitable for the preparation of both an ultrasound contrast agent and an ultrasound-controlled drug delivery system.

Conventional procedures for preparing liposomes do not allow for incorporation of a gas because the solubility of gas in water is low. According to Henry's Law, however, the solubility of a gas in a liquid is directly proportional to the pressure of that gas over the liquid. A solution is regarded as undersaturated, saturated or supersaturated when the pressure of the gas is less than, equal to or larger than the equilibrium saturation value in local temperature. Thus, if the pressure is increased, the gas molecule concentration in solution is increased, and when the pressure is lowered, the excess gas is released as vapor.

The pressure-freeze method of certain embodiments of the present invention is based on this principle. An essential role of freezing is to concentrate both gas and solute molecules so as to favor their encapsulation. Indeed, the basic phenomenon, that during freezing, air is released and often trapped as bubbles in the resultant ice, has been known for many years, and, moreover, that bubble formation in cells contributes significantly to freezing damage in long-term preservation of cells and tissues.

Exemplary steps of the methods of producing echogenic liposomes are provided below, particularly in Example 1 and FIGS. 1 and 7. Gas incorporation in liposomes is proportional to pressure. As noted above, this is to be expected from Henry's Law if gas uptake by the liposomes is proportional to the amount in solution at the first step. While this influences gas entrapment, it is the freezing step that has a large influence on dissolved gas and hence on gas encapsulation. While the present invention is not limited to any mechanism, it is believed that freezing probably serves two purposes, increasing the local concentration of dissolved gas and nucleating formation of small pockets of bulk gas phase. Gases, like other solutes, are more soluble in liquid water than in solid ice. Thus, as the ice crystals grow, dissolved gas is progressively displaced from ice to unfrozen solution, with the result that the dissolved gas becomes increasingly concentrated in the ever-diminishing volume of liquid solution. When the dissolved gas concentration becomes sufficiently high, a gas bubble may nucleate and grow. According to the nucleation theory, bubbles form when the difference between the total dissolved gas pressure and the ambient pressure in the surrounding liquid exceeds the Laplace pressure (the pressure created in a bubble due to the contraction of the surface under the influence of the surface tension).

Although it is clear that freezing expels the gas from the aqueous phase, it is unknown where the bubbles so expelled reside within the frozen dispersion. In order for the dispersion to become ultrasound-reflective, there must be pockets of air with surfaces of high acoustic impedance (as shown in FIG. 1). The gas might come out of solution in contact with the hydrophobic interior of the lipid bilayer, which has a relatively low surface tension against air; however, the effect of trehalose on air incorporation suggests a more complex process is involved. Trehalose, which functions as a cryo-protectant by favoring glass formation rather than crystallization (either of itself or of the water), supported much less echogenicity than did mannitol. Mannitol is rather distinctive among sugars in readily crystallizing out of solution upon cooling. Previously, it was proposed that freezing a mannitol solution inflicts damage upon liposomes. Consistent with that finding and based on nucleation theory is a suggestion made a number of years ago that the polar-nonpolar interface at the surface of damaged membranes may be the preferred site of nucleation of release of nitrogen bubbles in decompression sickness which affects divers who are rapidly decompressed.

Again, while the present invention is not limited to any particular mechanism, the following is believed to be part of the gas-containing liposome formation process. Although supersaturation of the liquid phase during ice formation should cause incipient air pockets to form, it is unlikely that this is the whole story, for, if it were, the echogencity should not be particularly low when samples are thawed prior to reducing the pressure back to ambient pressure. Under these conditions, the ice melts and the water produced is essentially degassed, so air associated with lipid (in all forms) will diffuse into this water. On the other hand, when the pressure is lowered first and the sample thawed second, the air concentration in the solution that melts initially is high because it contains most of the air that dissolved in the suspension upon pressurization. Because of its high solute (mannitol) content, the ice in the environment of the liposomes will melt first and immediately expose the lipid to ambient (1 atm) pressure. This initially melting phase is not only highly supersaturated with air, but it is also likely, as described in the preceding paragraph, to contain air pockets that will grow when exposed to ambient pressure. Hence, air will come out of solution, expanding the gas nuclei that presumably formed during freezing. The result is the formation of air pockets that are stabilized by a monolayer of lipid.

Furthermore co-encapsulation of gas (e.g., Xe) and an aqueous solute has advantages in drug delivery as it allows for release of liposomal contents by application of ultrasound. Since acoustically active liposomes also reflect ultrasound, it is possible to not only to localize the release of the drug according to the site of application of ultrasound, but also to image the therapeutic agent while it is being activated for delivery. Moreover, molecular targeting of the liposomes themselves is possible.

In addition to releasing liposomal contents and providing an image of the process, ultrasound can have effects on the tissue that synergize with drug delivery, namely cavitation effects of ultrasound which can facilitate access of the drug to its target. For example, prior methods found site-specific drug delivery can be achieved by destroying drug-filled contrast microbubbles in the target area with high-intensity ultra-sound (Porter et al., J Ultrasound Med 1996; 15(8): 577-84.). In addition, Shohet et al. (Circulation 2000; 101 (22):2554-6.) found that albumin-coated microbubbles could be used to effectively deliver an adenoviral transgene to rat myocardium via US-mediated microbubble destruction. Prior work has also found enhanced uptake of plasmid DNA in the presence of acoustically active liposomes and with the simultaneous application of ultrasound (Huang et al., Mol. Ther. 2003; 7 (5): 422 Part 2).

The sensitivity of echogenic liposomes to ultrasound stimulation may be able to be improved further by varying the liposomal composition, the encapsulated gas and/or the ultrasound application parameters. The lipid bilayer is held together by hydrophobic interactions that tend to endow it with self-sealing properties such that the lipid shell of a liposome rapidly reseals following surface alternations. It is therefore probable that changing the rigidity of the lipid membrane will affect its response to ultrasound. The choice of the optimal gas will involve both high volume in the liposomes and low rate of release in the blood stream. The most effective ultrasound pulses would seem to be a small number at the highest intensity that the tissue can sustain.

B. Targeting of Liposome

Targeted delivery is achieved by the addition of ligands without compromising the ability of liposomes to deliver their payloads. It is contemplated that this will enable delivery to specific cells, tissues and organs (e.g., specific sites in the brain). The targeting specificity of the ligand-based delivery systems is based on the distribution of the ligand receptors on different cell types. The targeting ligand may either be non-covalently or covalently associated with a nanoparticle, and can be conjugated to the nanoparticles by a variety of methods as discussed herein.

Examples of molecules that could be used to target liposomes of the embodiments include antibodies (or fragments thereof) and apatmers. Alternatively or additional it is contemplated that cell-penetrating peptides may be used to deliver liposomes directly into cells.

III. Pharmaceutical Compositions and Routes of Administration

Where clinical application of liposomes (e.g., liposomes comprising gases) is undertaken, it will be necessary to prepare the liposome complex as a pharmaceutical composition appropriate for the intended application. Generally, this will entail preparing a pharmaceutical composition that is essentially free of pyrogens, as well as any other impurities that could be harmful to humans or animals. One also will generally desire to employ appropriate buffers to render the complex stable and allow for uptake by target cells. Aqueous compositions of the present invention comprise an effective amount of Xe encapsulated in a liposome as discussed above, further dispersed in pharmaceutically acceptable carrier or aqueous medium. Such compositions also are referred to as inocula. The phrases "pharmaceutically" or "pharmacologically acceptable" refer to compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms. The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters. Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions generally will take the form of solutions or suspensions.

The therapeutic compositions of the present embodiments may include classic pharmaceutical preparations. Administration of therapeutic compositions according to the present invention will be via any common route so long as the target tissue is available via that route. In this case, intravenous injection or infusion may be preferred. Such compositions would normally be administered as pharmaceutically acceptable compositions that include physiologically acceptable carriers, buffers or other excipients.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired.

An effective dose range of a therapeutic can be extrapolated from effective doses determined in animal studies. In general a human equivalent dose (HED) in mg/kg can be calculated in accordance with the following formula (see, e.g., Reagan-Shaw et al., *FASEB J.*, 22(3):659-661, 2008, which is incorporated herein by reference):

$$\text{HED (mg/kg)} = \text{Animal dose (mg/kg)} \times (\text{Animal } K_m/\text{Human } K_m)$$

Use of the $K_m$ factors in conversion results in more accurate HED values, which are based on body surface area (BSA) rather than only on body mass. $K_m$ values for humans and various animals are well known. For example, the $K_m$ for an average 60 kg human (with a BSA of 1.6 $m^2$) is 37, whereas a 20 kg child (BSA 0.8 $m^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are peculiar to each individual. Nonetheless, a calculated HED dose provides a general guide. Other factors affecting the dose include the physical and clinical state of the patient, the route of administration, the intended goal of treatment and the potency, stability and toxicity of the particular therapeutic formulation. For the instant embodiments, it is envisioned that the amount of therapeutic liposome (e.g., Xe-ELIP) dose in a human (adult) will be greater than about 0.568 mg/kg. For example, the human dose range can be between about 0.6 and 3.0 mg/kg, between about 0.8 and 2.8 mg/kg, or between about 1.0 and 2.5 mg/kg. In some specific aspects Xe-ELIP is administered to a human subject in a dose of between about 1.14 mg/kg and about 2.27 mg/kg.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Xe-ELIP Production and Experimental Methods

Xe-FLIP Production

Figure 7:
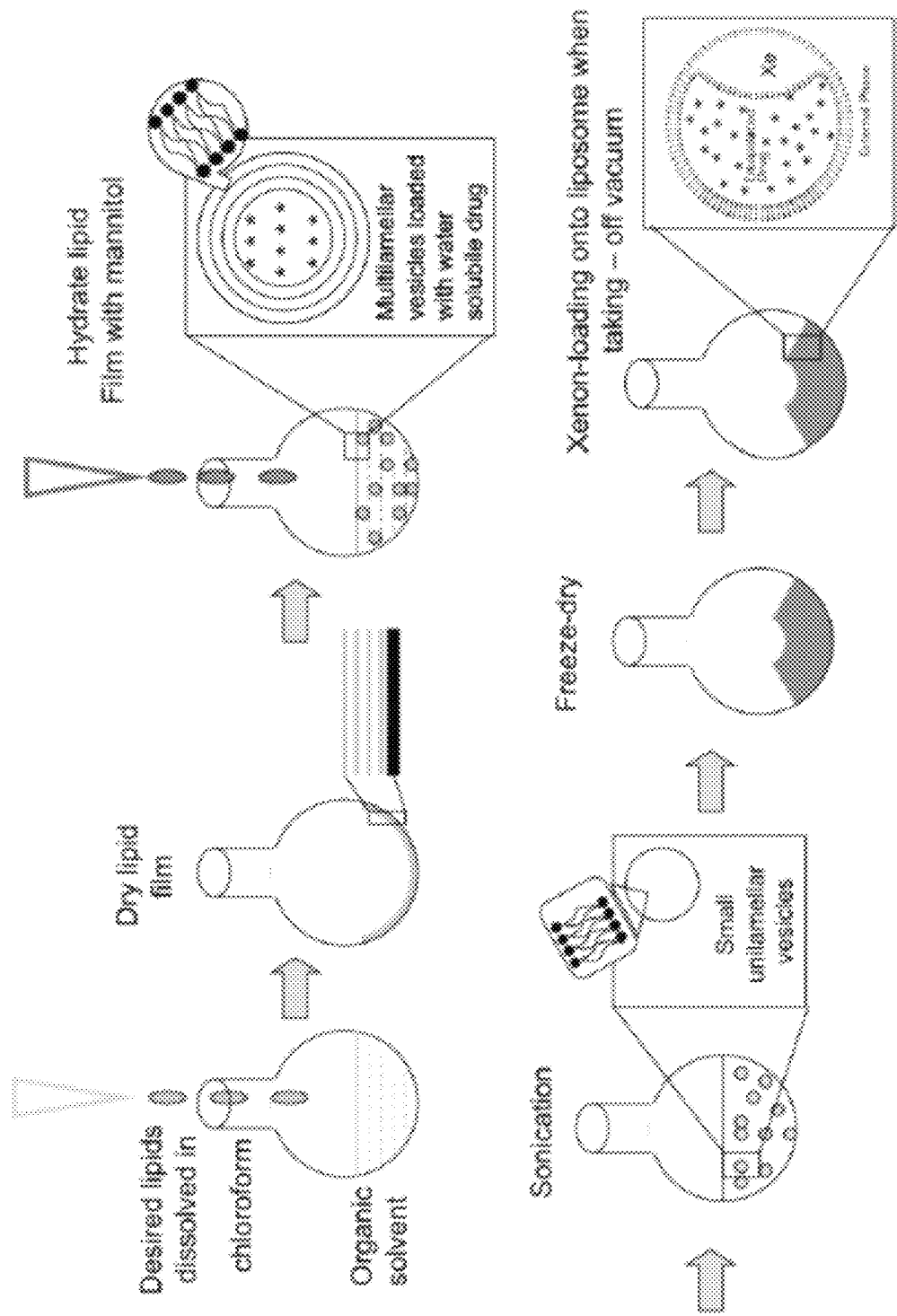
FIG. 7: Schematically shown is an example protocol for the preparation of echogenic liposomes of the embodiments.

Xenon-ELIP were produced using the freeze thaw protocol that is schematically illustrated in FIG. 7 (see also, U.S. Pat. No. 7,976,743, incorporated herein by reference). Briefly, liposomes were composed of L-α-phosphatidylcholine (egg PC), 1,2-dipalmitoyl-sn-glycero-3-phosphocholine (DPPC; Avanti Polar Lipids, Alabaster, Ala.); 1,2-dipalmitoyl-sn-glycero-3-phosphoethanolamine-N-[methoxy(polyethylene glycol)-2000] (16:0 PEG2000 PE) and cholesterol (Sigma, St Louis, Mo.). Five milligrams of lipids was mixed in chloroform, and the solvent was evaporated with argon in a 50° C. water bath to form a thin film on the glass vial. The lipid film was placed under vacuum for 4 to 6 hours for complete solvent removal. The dried lipid film was hydrated with 0.32 mol/L mannitol to a concentration of 10 mg lipid per milliliter, followed by sonication for 5 minutes. The sonicated liposomes were transferred to a 2-mL glass vial with a cap sealed with a Teflon-rubber septum. Six milliliters of Xe (100%) (Concorde Specialty Gas Inc, Eatontown, N.J.) was injected into the glass vial through the Teflonrubber septum with a 12-mL syringe attached to a 27-guage-½-inch needle (note that at this stage other gases and/or gas mixtures may be incorporated). The pressurized liposomal dispersion was frozen at −70° C. with dry ice for at least half an hour. The liposomal dispersion was allowed to thaw after the vial was unpressurized by removing the cap. The structure and gas retention properties of Xe-ELIP are shown in FIG. 1.

Rat Model of MCA Occlusion

All animal experiments were approved by the Animal Welfare Committee at The University of Texas Health Science Center at Houston. Male Sprague-Dawley rats (260-280 g, Harlan Laboratories Inc., Indianapolis, Ind.) were fasted for 24 hours with free access to water prior to surgery. Before surgery, anesthesia was induced by placing rodent in a sealed induction chamber (ask Melanie) for 5 minutes with a continuous flow of isoflorane. Marcaine (2 mg/kg) was injected subcutaneously at the surgical site to provide topical analgesia. Cerebral ischemia was induced by occluding the right middle cerebral artery (MCA) for 2 hours using the intraluminal suture method described previously (Britton, et al. 2010, incorporated herein by reference). In brief, a 1 mm diameter burr hole was made in the skull to facilitate local cerebral perfusion (CP) measurement before occluding the MCA. Next, the right common carotid artery (CCA) was exposed through a midline neck incision. The right external carotid artery (ECA) was then ligated close to its distal end. The internal artery was isolated and separated from adjacent tissues. A fabricated 25-cm 4-0 nylon monofilament was advanced from the right ECA and inserted into the right MCA for 2 hours to provoke ischemia. Interruption of local blood flow through the MCA was verified with a laser Doppler flowmeter placed over the ischemic area at 2 mm posterior and 6 mm lateral to the bregma. In all experiments, body temperature was maintained at 37° C. during ischemia. A polyethylene catheter was introduced into the right femoral artery for pressure recordings.

Determination of the Therapeutic Time Window

Animals were randomly divided into four groups (n=8 in each group), (1) no treatment group—MCA occlusion only; (2) treatment group "a"—Xe-ELIP administration 10 min after reperfusion; (3) treatment group "b"—Xe-ELIP administration 60 min after reperfusion; (4) treatment group "c"—Xe-ELIP administration 180 min after reperfusion. All rats in each treatment group were administrated 200 µl of Xe-ELIP over a period of 4 minutes by cannulating the right internal carotid artery with modified PESO tubing. The ICA was exposed to 1-MHz continuous wave ultrasound at a peak-to-peak pressure amplitude of 0.18 MPa (1-W/cm2 dial setting) during Xe-ELIP administration. Neurological assessments were conducted over the following three days. On the third day after MCAO the infarct volume was determined by 2% 2,3,5-triphenyltetrazolium chloride (TTC) staining.

Determination of the Dose Dependence and Effect of Xe-ELIP Administrations

Animals were randomly divided into four groups (n=8 in each group), (1) no treatment group—MCA occlusion only; (2) treatment group "a"—received a 100 µl dose of Xe (10 mg Xe-ELIP/ml); (3) treatment group "b"—received a 200 µl dose of Xe-ELIP (10 mg Xe-ELIP/ml); (3) treatment group "c" received a 400 µl dose of Xe-ELIP (10 mg Xe-ELIP/ml). All rats in each treatment groups received Xe-ELIP 60 min after reperfusion by cannulating the right internal carotid artery with modified PESO tubing. The ICA was exposed to 1-MHz continuous wave ultrasound at a peak-to-peak pressure amplitude of 0.18 MPa (1-W/cm2 dial setting) during Xe-ELIP administration. The infarct volume was determined 3 days after MCAO by TTC staining. Neurological assessments were conducted over the following three days. On the third day after MCAO the infarct volume was determined by 2% TTC staining.

Neurologic Assessment

All behavioral tests in mouse were conducted in a quiet and low-lit room by an observer blinded with respect to the treatment groups. At days 1, 2 and 3 after surgery, each animal was tested for motor function and neurologic outcomes by recording limb placing, beam walking and grid walking abilities.

Limb placement was assessed by observing the animal's ability to lift its head and extend its forelimbs toward a table while the animal was suspended over the table by its tail (zero score—no response; score of 1-10 when response was sluggish or delayed; score of 2 when response was rapid and fully executed). The ability to walk across a beam (2.5×2.5× 80 cm) was assessed by observing the ability to maintain balance while navigating across the beam. The response scores were assigned as follows: score 0-traversed the beam with no foot slip; score 1—traversed with grasping of the lateral side of the beam; score 2—showed difficulty crawling across the beam but able to traverse; score 3—required a more than 10 seconds to traverse the beam due to difficulty in walking; score 4—unable to traverse the beam; score 5—unable to move the body or any limb on the beam; score 6—unable to stay on the beam for more than 10 seconds. Grid walking ability was assessed by placing the animal on a stainless steel grid floor (20 cm×40 cm with a mesh size of 2 cm×2 cm). The total number of steps was counted up to a maximum of 50 steps. The number of foot fault errors as defined by the misplacement of a forelimb or hindlimb that fell through the grid was recorded.

Infarct Volume Measurement

Animals were sacrificed on the third day following neurological assessment. Brains were harvested. Using a Jacobowitz brain slicer, 2 mm thick coronal sections were cut prior to staining with 2% 2,3,5-triphenyltetrazolium chloride (TTC) in PBS for 20 minutes at 3rC for infarct volume determination. Stained sections were transferred to 10% phosphate buffered formalin for storage. Sections were photographed with a Canon G7 10.0 megapixel camera fitted on a Polaroid land-tripod at an object distance of 8.5 cm. Images were transferred and analyzed with Image Pro-Plus to calculate infarct volumes. Infarct volume was calculated by measuring infarct areas on evenly sliced (1 mm) brain sections and adding them together (Simpson's rule). Normalized infarct volume with respect to whole brain volume was calculated by dividing the volume of TTC unstained (infarcted) tissue by that of the whole brain.

Gel Electrophoresis and Immunoblotting

Animals were subjected into three groups: 1) sham surgery without ischemia; 2) MCAO for 2 hours without treatment; and 3) MCAO for 2 hours and reperfusion for 1 hour following Xe-ELIP (400 µl) administration intra-artery. Brain tissue slices were collected and homogenized in 1 ml of RIPA (Radio Immuno Precipitation Assay) buffer (Cell Signaling Technology, MA, USA) containing the protease inhibitors, phenylmethlylsulfonyl fluoride (PMSF, 1 mM), and phosphatase inhibitor cocktail (Santa Cruz Biotechnology, CA, USA). Brain tissues were harvested at 7 and 24 hours after stroke onset. Whole cell protein was extracted and sonicated with SONICS Vibra Cell (SONICS & MATERIALS Inc, CT, USA) for three times. The supernates were collected and protein concentration was measured. Equal amount of protein (80 µg) were loaded and separated on 12% SDS-Polyacrylamide gels with electrophoresis of Tris-glycine running buffer system for 2 hours, and then transferred to a polyvinylidene difluoride (PVDF) membrane (Millipore, MA, USA). After blocking in Non Mammalian Blocking Reagent (LI-COR Biosciences, NE, USA) without tween-20 for 1 hour, the membranes were incubated with primary antibodies of BDNF (1:250, Santa Cruz Biotechnology, CA, USA), phosphorylated AKT (1:250, Cell Signaling Technology, MA, USA) or total Akt (1:500, Cell Signaling Technology, MA, USA), and Phospho-ERK1/2 (1:250, Cell Signaling Technology, MA, USA) or Erk1/2 (:500, Cell Signaling Technology, MA, USA) at 4° C. overnight. After washing membranes with Tris-buffered saline containing 0.1% Tween-20 (TBS-T), the membrane was incubated with IRDye 800CW Dky Anti-Rabbit IgG secondary antibody (H+L) (LI-COR Biosciences, NE, USA) at room temperature for 1 hour. After extensive washes (Rinse twice and wash 3 times×5 min) in TBS-T 0.1%, blots were visualized by odyssey infrared imaging system (LI-COR Biosciences, NE, USA). To ensure equivalent protein loading, membranes were reprobed with Anti b-actin (Sigma, MO, USA) for 1 hour at room temperature, and then incubated with IRDye 680 L T Gt Anti-Mouse lgG (H+L) (LI-COR Biosciences, NE, USA) for 1 hour. Membranes were scanned using same odyssey infrared imaging system. The optical densities of all protein bands were analyzed by using NIH ImageJ software. All target proteins were quantified by normalizing to b-actin and calculated as fold of the corresponding control group.

Statistical Analyses

Nonparametric statistical analyses were performed by the Wilcoxon rank test for two groups or Kruskal-Wallis analysis of variance (ANOVA) for multiple groups, and reported as mean and standard deviation for most experiments. When differences were detected in global comparison, the multiple comparisons of mean ranks for all groups were performed for all pairwise comparisons. Neurologic outcome comparison between the treatment groups was reported as median and quartiles. Statistica (Version 9, StatSoft Inc., Tulsa, Okla.) software were utilized for statistical analyses. A $p<0.05$ was considered significant.

Example 2—Xe-ELIP as Therapeutic for Stroke

The dose dependency Xe-ELIP therapy was first investigated by injecting Xe-ELIP at dosage range of 1-4 mg/rat (3.5, 7 and 14 mg/kg) at 3 hours after stroke onset on a Male Sprague-Dawley rat model with occlusion (for 2 hours) of the right transient endovascular filament middle cerebral artery (MCAO). Treatment groups that received 7 mg/kg or 14 mg/kg of Xe-ELIP at 3 hours after stroke onset reduced the normalized infarct size to 6.0±2% (p=0.04) and 3.7±2% (p=0.002) respectively (FIG. 4a-e). This study demonstrates that Xe-ELIP administered within 3 hours after stroke onset at a dosage larger than 2-4 mg (e.g., 7 mg/kg or greater) provide best neuroprotection.

Behavioral assessments of neurological damage were conducted by recording limb placing, beam walking and grid walking abilities in a quiet and low-lit room in an observer blinded manner at days 1, 2 and 3 after surgery. Results are shown in FIG. 4f-h demonstrate very significant behavioral improvement in animals treated with 7 mg/kg or 14 mg/kg.

The therapeutic time window of Xe-ELIP was then further investigated on both rat filament MCAO and thrombotic MCAO model. Xe-ELIP was administrated through the ascending right common carotid artery at 2, 3, and 5 hour after stroke onset (10 min, 1 hour and 3 hour after reperfusion) on filament MCAO model. In the non-treatment group, a large infarction developed and predominantly involved the cerebral cortex and striatum with normalized infarct volume of 16±5.2% (228±74 mm$^3$) of whole brain (FIG. 2a, e). Xe-ELIP administration at 10 min and 2 hours after stroke onset reduced the normalized infract size from 15±5.1% (control) to 4.9±1.2% (p=0.005) and 6.0±3.4% (p=0.002), respectively (FIG. 2a-e). There was no difference in core body temperature between the groups during MCA occlusion and the initial hours of reperfusion.

Behavioral assessment of neurological damage were conducted by recording limb placing, beam walking and grid walking abilities in a quiet and low-lit room in an observer blinded manner at days 1, 2 and 3 after surgery. The group with Xe-ELIP administered at 3 hours after stroke on set demonstrated marginal improvements in performing behavioral tasks. Both Xe-ELIP administered at 10 minutes and 1 hour groups demonstrated improved performance in all behavioral tests from day 1 with marked improvements in all tests by day 3 (FIG. 2f-h). It was demonstrated that Xenon protected neuron damage as a glutamate receptors (NMDA) antagonist while the excitotoxic effect caused by excessive extracellular glutamate accumulation was absorbed in an early event of ischemia.

Figure 6A:
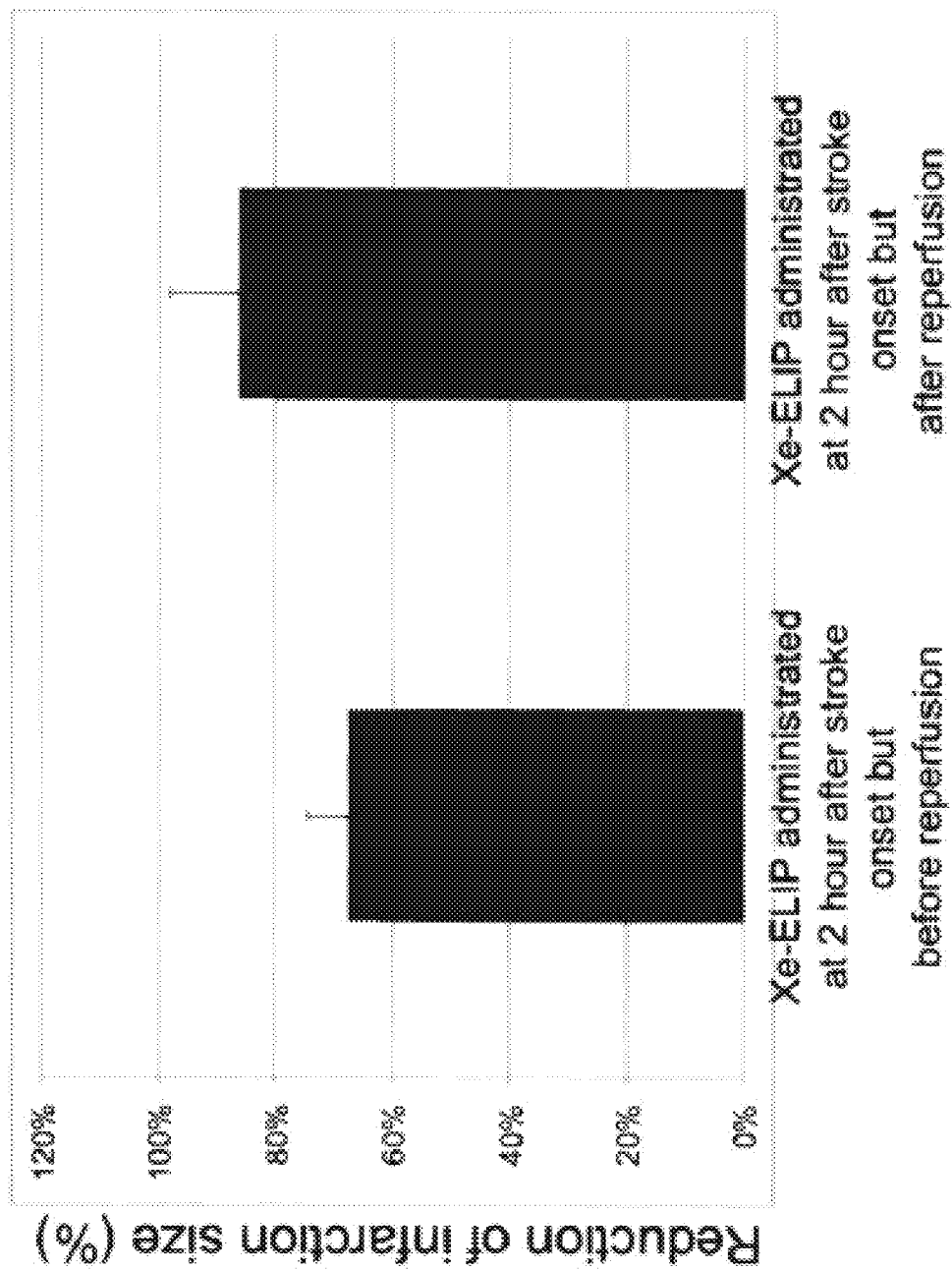
FIG. 6a-b: (a), Xe-ELIP provides neuroprotective effects when administered either before or after restoring blood flow. (b), Percent clot mass loss in animals after the indicated treatments with Xe-ELIP and/or tPA.

The therapeutic time window of Xe-ELIP at 2 hour after stroke onset (10 min after reperfusion) showed therapeutic effect. In the clinical setting, the tPA administration for stroke treatment is limited by its narrow therapeutic time window. Although 85% of strokes are due to occlusion of cerebral artery by a circulating clot, 15% of strokes are hemorrhagic. IV tPA cannot be administrated until the exclusion of hemorrhage stroke from thrombotic stroke. Thus, neuroprotective agent administration before IV tPA to prolong tPA therapeutic time window is a very promising clinical relevant strategy. Thus the neuroprotective effect of Xe-ELIP administration was further investigated at 2 hour after stroke onset but before and after reperfusion. The reduction of brain infarct by Xe-ELIP before and after treatment is shown in FIG. 6a. Xe-ELIP before reperfusion and after reperfusion reduced the normalized infract size by 86±12% and 67±7%, respectively.

Figure 6B:
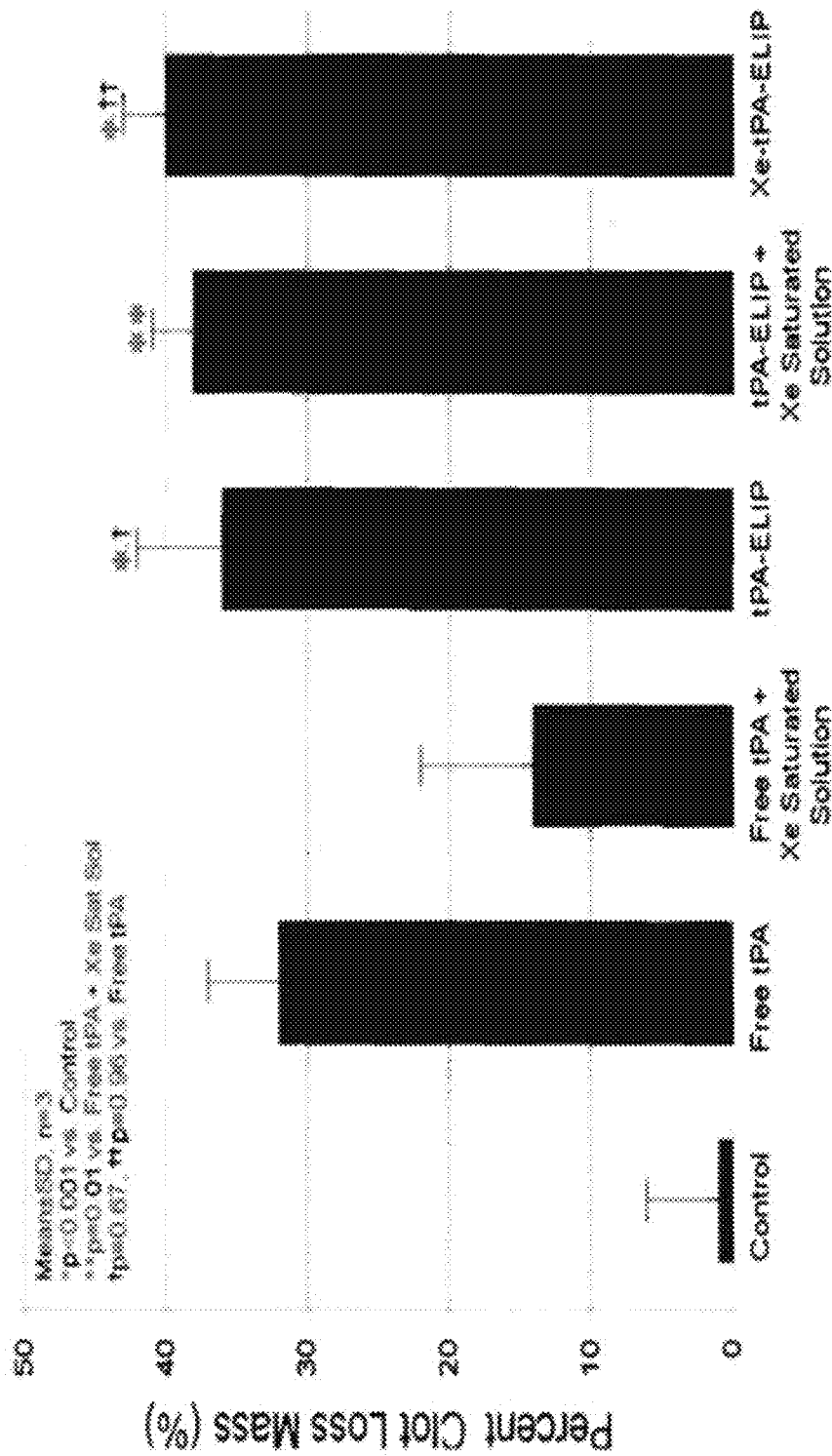

The administration of tPA within 4.5 h of ischemic stroke onset remains the only treatments that have been shown to have clinical benefit. Neuroprotective combination therapy may minimize the harmful effects of ischemic neuronal damage. To test the effect of Xe-ELIP on tPA activity, thrombolytic efficiency of tPA in the present of Xe-ELIP was compared with tPA alone on porcine blood clot. The thrombolytic effect of tPA was inhibited after 30 minute incorporation with free Xe (Xe saturated solution). When tPA was incorporated with Xe-ELIP, it had the same thrombotic effect as tPA alone. This demonstrated a protective effect of ELIP on Xe from interaction with tPA (FIG. 6b).

The therapeutic effect of Xe-ELIP in a rat embolic stroke model was next investigated. Thrombotic strokes were induced in male Sprague-Dawley rats (n=16) by injecting a 13 mm long blood clot into the middle cerebral artery. In the treatment group, tPA (10 mg/kg) was infused intravenously at 2 hours after the onset occlusion. Xe-ELIP was administrated intravenously before IV tPA. Continuous wave ultrasound (1 MHz, 50% duty cycle, 0.5 W/cm$^2$) was applied to trigger Xe release from ELIP during the 5 min of Xe-ELIP administration. The thrombotic stroke control group without any treatment exhibited the largest damage and infarct size (17±5% of the whole brain) (FIG. 5a-e). The tPA treatment reduced the damage and the infarct size to 5.2±0.4% (p=0.025 vs. stroke). The tPA treatment in combination with Xe-ELIP further reduced infarct size to 1.5±0.4% (p=0.05 vs. tPA group). Behavioral deficit correlated inversely with infarct volume. Regional blood flow velocity monitored by a laser Doppler flow meter was similar in both tPA and tPA+Xe-ELIP treatment groups (FIG. 5f-h). This study demonstrated a neuroprotective effect of ELIP encapsulated xenon released by application of 1 MHz ultrasound. Xe-ELIP can be used in combination with tPA without affecting tPA thrombolytic activity. Death rates resulting from the treatment conditions are shown in Table 1 below.

TABLE 1

| Group | Death rate | Occlusion rate | Reperfusion rate after IV tPA |
|---|---|---|---|
| Sham | 0 | 0 | — |
| Stroke | 60% | 58 ± 9% | — |
| Stroke + tPA | 31% | 50 ± 8% | 21 ± 17% |
| Stroke + Xe-ELIP + tPA | 29% | 53 ± 6% | 23 ± 14% |

The effects of Xe-ELIP on BDNF expression and apoptosis was also assessed (see, e.g., FIG. 3). Western blot analysis of BDNF (a), phos-Akt (b) and phos-ERK (c) in cerebral cortex tissue 24 h after stroke showed that Xe increased the expression of BDNF (d), total Akt (e) and phos-ERK (f) (FIG. 3a-f). TUNEL staining in the penumbral region of brain sections from the sham-operated group (g), stroke group (h) and stroke with Xe-ELIP treatment group (i) showed reduction of apoptosis in Xe-ELIP-treated animals (FIG. 3). The Western blots and photomicrographs of apoptosis are representative of three independent experiments. Data are means±SD.

Example 3—Xe-ELIP Provides Effective Protection in Hemorrhagic Stroke

Xe-ELIP compositions were produced as detailed in Example 1. To assess the efficacy Xe-ELIP a rat model of subarachnoid hemorrhage was employed. Briefly, healthy male Sprague Dawley rats (Harlan Laboratories Inc., Indianapolis, Ind.) weighing between 260-280 grams were obtained. All surgical procedures were performed under dissecting microscope on anesthetized animal. The right external carotid artery was isolated and a 4.0 fabricated sharp nylon monofilament was introduced through the internal artery to perforate the middle cerebral artery. The monofilament was immediately retracted to resume blood flow to the middle cerebral artery. The blood flow was monitored to confirm the bleeding.

Following the induction of bleeding Xe-ELIP (600 µl, 10 mg/ml) was infused for 5 minutes through the femoral vein with simultaneous ultrasound application (0.5 MPa) over the internal carotid artery to trigger the release of xenon from circulating Xe-ELIP into brain. Neurological and behavioral tests were conducted for 3 days following surgery. Animals were sacrificed for SAH grading to evaluate the degree of bleeding, brain water contain to evaluate the edema and TUNEL staining to check the apoptosis, on the third day following neurological and behavior assessments.

Figure 8:
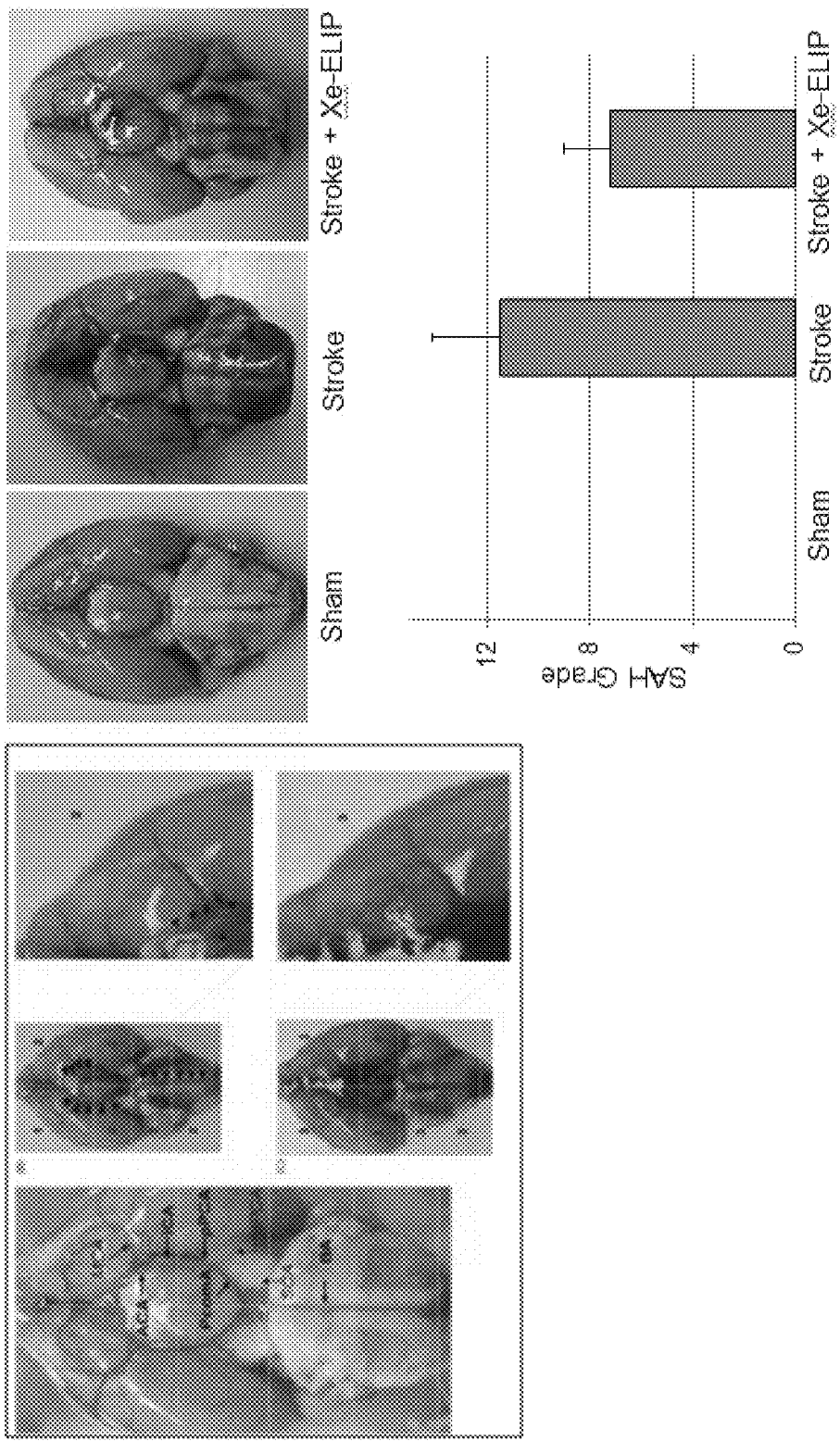
FIG. 8: Results show that Xe-ELIP decreases the bleeding in a filament perforation subarachnoid hemorrhage (SAH) rat model.
Figure 9:
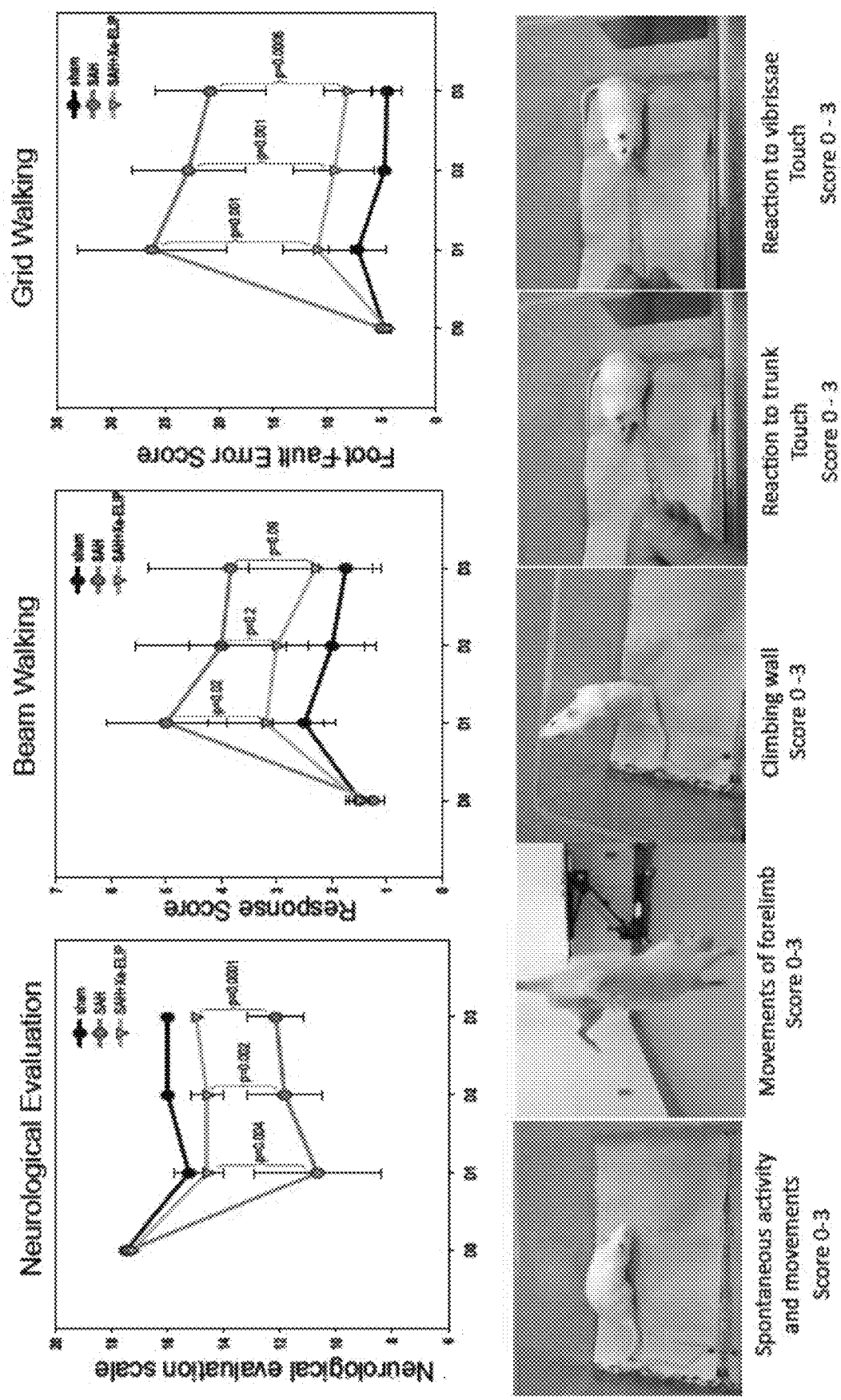
FIG. 9: Results show that Xe-ELIP improves the general neurological evaluation scales and motor function of SAH rats.
Figure 10:
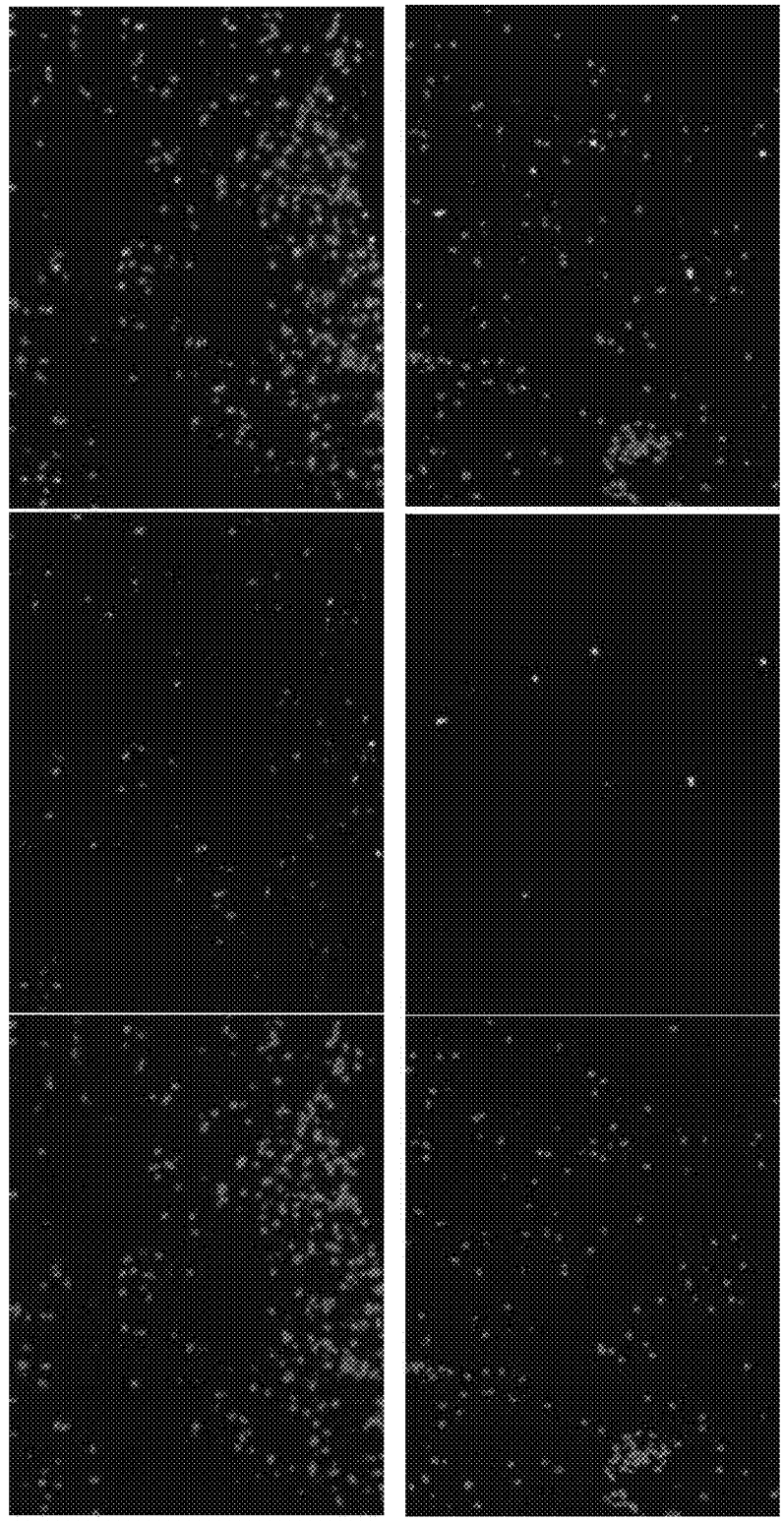
FIG. 10: Results show that Xe-ELIP prevents neuronal apoptotic cell death. Representative photomicrographs show TUNEL staining of brain sections from hemorrhage stroke group (upper panels), and hemorrhage stroke with Xe-ELIP treatment group (bottom panels). The left panels are DAPI stain of total cells. Center panels are tunnel stain of apoptotic cells. Right panels are merged images.
Figure 11:
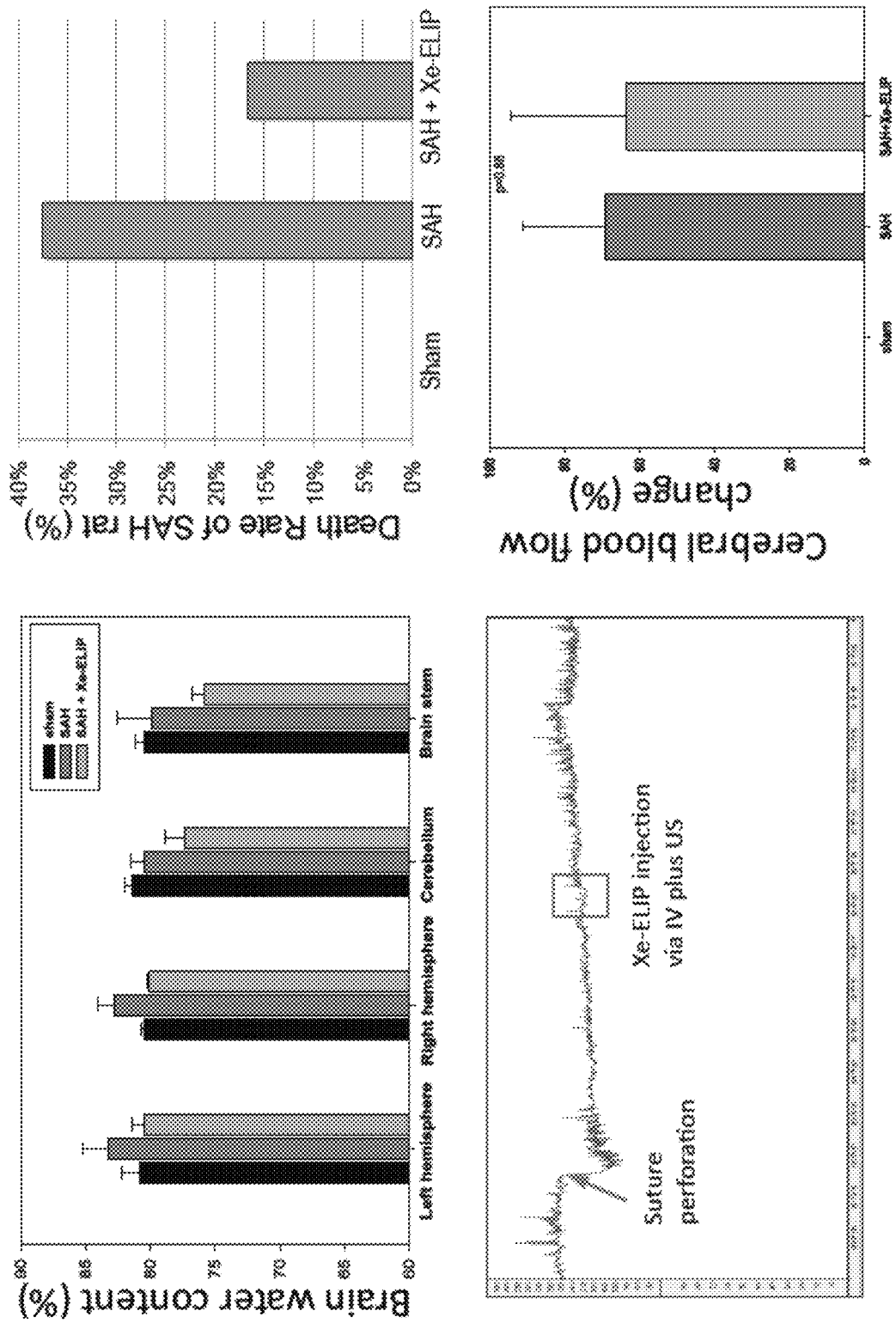
FIG. 11: Results show that Xe-ELIP decreases the mortality rate of SAH rats but does not greatly affect brain edema and cerebral blood flow.

Results from the physical examination of brain tissue are shown in FIG. 8. For scoring the basal cistern was divided into six segments. Bleeding was assessed in each of these segments and scored from 0 to 3 (0: no SAH; 1: minimal SAH; 2: moderate blood clot with recognizable arteries; 3: blood clot obliterate the arteries). The total scores were added and the severity of bleeding was scaled as: 0-7: mild SAH; 8-12: moderate SAH; 13-18: severe SAH.Xe-ELIP decreases the bleeding in filament perforation subarachnoid hemorrhage (SAH) rat model Results of behavioral testing of the treated rats are shown in FIG. 9. Lower panel illustrates the array of behavioral tests to which animals were subject. Results of neurological evaluation, beam walking and grid walking are shown in the graphs of the upper panel. In each case rats treated with Xe-ELIP performed significantly better than untreated rats. Indeed, microscopic examination of brain sections using TUNEL staining (FIG. 10) showed that brain sections from hemorrhage stroke group, upper panels, had significantly more apoptotic cells as compared to the hemorrhage stroke with Xe-ELIP treatment group, bottom (compare center panels). Perhaps most importantly, Xe-ELIP treatment decreased the death rate of SAH rats but did not show significant effects on brain edema and cerebral blood flow (FIG. 11). Brain edema is the major life-threatening complication of stroke. It is frequently associated with subarachnoid hemorrhage, vasospasm and ischemic reperfusion damage. The results shown here demonstrate that ELIP formulations containing only one gas (Xe) does not affect the brain edema and vasoactivity. It has been shown that hydrogen administration after stroke can eliminate the brain edema by decreasing blood-brain barrier permeability, and $H_2S$ inhibits vasospasm by anti-inflammatory effect. Thus, in some aspects, formulations that co-encapsulate hydrogen gas and/or hydrogen sulfide gas with Xe-ELIP would have added effect on brain edema and cerebral vasospasm.

Example 4—$H_2$ and $H_2S$ Enhance Xe-ELIP Efficacy

Studies were next undertaken to evaluate co-encapsulation of Xe with hydrogen or hydrogen sulfide into ELIP. ELIP were composed of phospholipids and cholesterol and were produced as detailed in Example 1. In this case, however, gas mixtures of 30% hydrogen+70% xenon or 1% hydrogen sulfide+99% xenon were loaded onto ELIP by the pressurized-freeze method in addition to use of 100% Xe.

Figure 12:
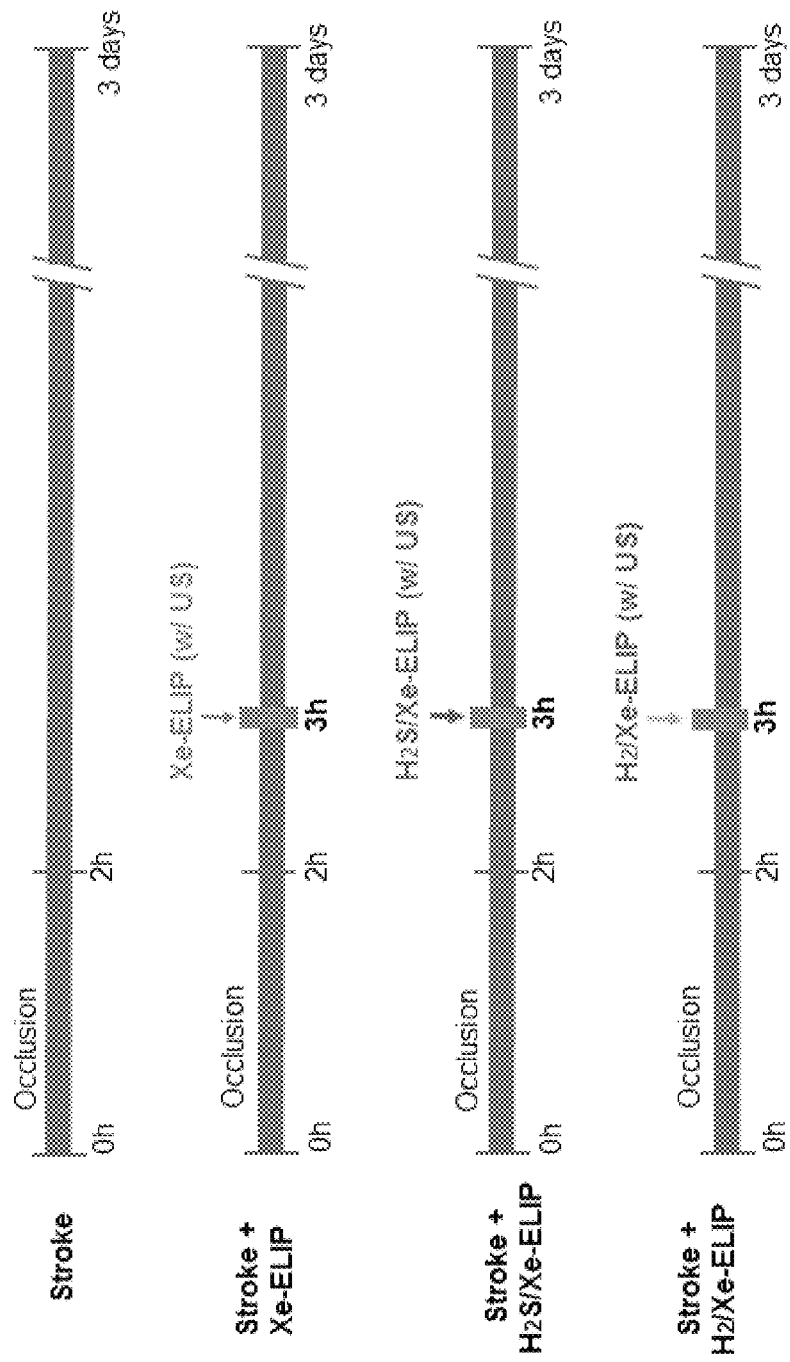
FIG. 12: Schematics show time lines for the experiments of Example 4.

The design of efficacy experiments is graphically represented in FIG. 12. As indicated, in order to test the therapeutic effect of $H_2$/Xe-ELIP or $H_2S$/Xenon ELIP, 400 µl of each (in additional Xe-ELIP alone) were administered into Sprague-Dawley rats intravenously separately after (at 3 h) right middle cerebral artery occlusion. One-megahertz low-amplitude (0.18 MPa) continuous wave ultrasound directed onto the internal carotid artery was used to trigger gas release from circulating Xe-ELIP.

Animals were then subjected to behavioral testing and their brains examined to assess the physical damage present. As shown in FIGS. 13a and b, both addition of $H_2$ and $H_2S$ further increased the ability of Xe-ELIP to reduce the normalized infarct volume in the brains of treated rats. As shown in FIG. 13c, addition of $H_2S$ further increased the ability of Xe-ELIP to reduce the number of TUNEL positive cells in the brains of treated rats, indicated reduce neuron cell damage. Analysis of neutrophil invasion across the vascular wall in the brains of treated rats showed decreased invasion following Xe-ELIP treatment, which was enhanced by $H_2S$. Inhibition of neutrophil transfer across the vascular wall is one potential mechanism for $H_2S$/Xe-ELIP neurovascular unit protection.

Perhaps more importantly animals treated Xe-ELIP combined with of $H_2$ or $H_2S$ also tended to perform better in behavioral testing that included limb placement, beam walking and grid walking (FIG. 14). In particular, the combined therapy was show to be significantly better in improvement of grid walking ability as compared to both control (untreated) rats and rats treated with Xe-ELIP alone.

Figure 15:
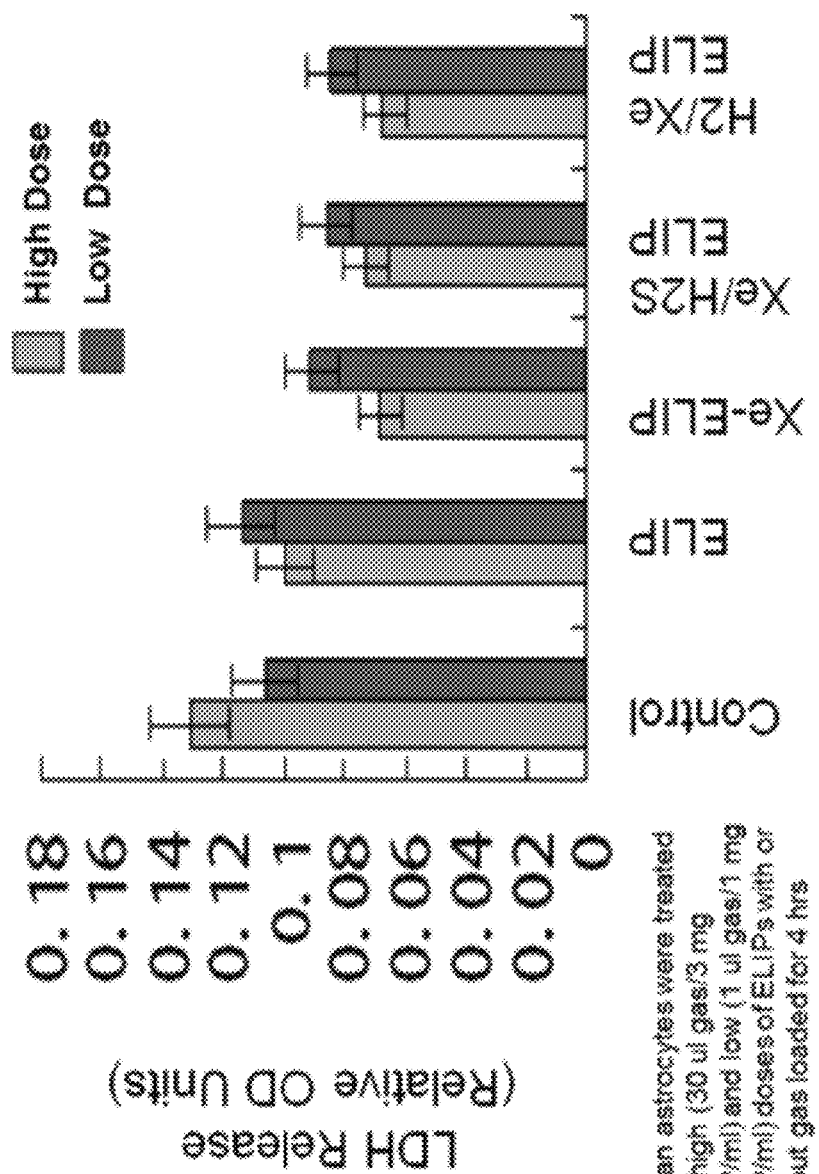
FIG. 15: Graphs show the results of the tests of efficacy of Xe-ELIP reagents in the protection of human brain astrocytes against the H$_2$O$_2$ (10 mM) cytotoxicity using lactate dehydrogenase (LDH) release assays.

Example 5—Xe-ELIP Protection of Culture Human Brain Astrocytes Against Hydrogen Peroxide ($H_2O_2$) Cytotoxicity or Oxidative Stress Human brain astrocytes play a key role in maintaining nerve cell function and survival against oxidative stress. Exposure of cultured human brain astrocytes to $H_2O_2$ causes significant damages to the cells, and caused them to release large amounts of LDH. However, pretreatment of the brain cells with Xe-ELIP reagents markedly reduced LDH release (FIG. 15), indicating a protective effect of Xe-ELIP on the brain cells injured by the oxidative stress. No or little protective effect was found in the cells treated with ELIP alone or control media (FIG. 15).

Example 6—Xe-ELIP has No Cytotoxicity to Murine Stem Cells

Figure 16:
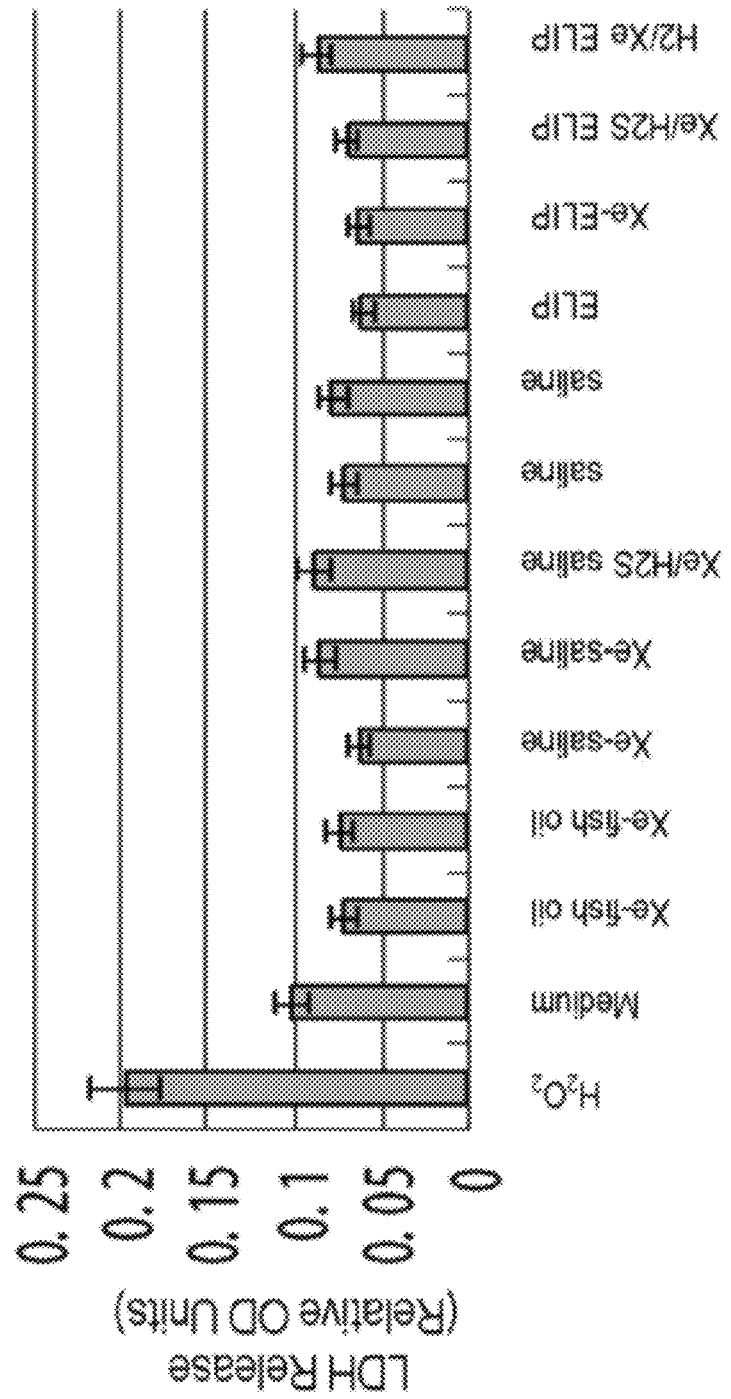
FIG. 16: Graphs show the results of the tests of Xe-ELIP cytotoxicity in stem cells. H$_2$O$_2$ but not the Xe and Xe-ELIP reagents cause significant LDH release in murine embryonic stem cells. Cells were treated with Xe-reagents (3 mg ELIP/30 µl gas/ml) and control medium for 4 hours, and 2 hours before the end of cultures; 10 mM H$_2$O$_2$ was added.

Murine embryonic stem cells were examined for their growth and survival when they were treated with or without $H_2O_2$ in the presence or absence of Xe-ELIP. The cell viability was determined by assessing the release of LDH. In the presence of ELIP loaded with or without Xe or other gases, LDH levels in the cultures remained significant levels (FIG. 16). By contrast, addition of $H_2O_2$ (10 mM), significant LDH release was found within 2 hours of exposure to the oxidative stress agent $H_2O_2$ (FIG. 16).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,162,282
U.S. Pat. No. 4,310,505
U.S. Pat. No. 4,533,254
U.S. Pat. No. 4,728,575
U.S. Pat. No. 4,728,578
U.S. Pat. No. 4,737,323
U.S. Pat. No. 4,921,706
U.S. Pat. No. 5,030,453
U.S. Pat. No. 5,612,057
U.S. Pat. No. 5,855,911
U.S. Pat. No. 5,858,399
U.S. Pat. No. 5,962,016
U.S. Pat. No. 6,413,544
U.S. Pat. No. 6,680,068
U.S. Pat. No. 6,770,291
U.S. Pat. No. 7,976,743
U.S. App. No. 2004/0208921
PCT/US85/01161
PCT/US89/0504
GB 2193095 A
WO02/100435A1
WO03/015757A1
WO04/002453A1
WO04/029213A2
Bangham et al., *J. Mol. Biol.*, 13:238-252, 1965.
Britton, et al., *Circulation*, 122:1578-1587, 2010.
Cheng et al., *Invest. Radiol.*, 22:47-55, 1987.
Deamer and Uster, Liposome preparation: methods and mechanisms, In: *Liposomes*, (Ostro M. J., Ed.), Chapter 1, Marcel Dekker, New York, 1983.
Farhood et al., *Biochim. Biophys. Acta*, 1235:289-295, 1995.
Ghosh and Bachhawat, In: Liver Diseases, Targeted Diagnosis and Therapy Using Specific Receptors and Ligands, We et al. (Eds.), Marcel Dekker, New York, p. 87-104, 1991.
Gregoriadis, In: Drug Carriers in Biology and Medicine, Gregoriadis (Ed.), p 287-341, 1979.
Hope et al., *Biochim. Biophys. Acta*, 812:55, 1985.
Huang et al., *Mol. Ther.*, 7(5):422 Part 2, 2003.
Liposome Technology, CRC Press, 1984.
Mayer et al., *Chem. Phys. Lipids*, 40:333-346, 1986.
Mayhew et al., *Biochim. Biophys. Acta*, 775:169, 1984.
Mayhew et al., *Exp. Cell Res.*, 171:195-202, 1987.
Porter et al., *J. Ultrasound Med.*, 15(8):577-584, 1996.
Reagan-Shaw et al., *FASEB* 22(3):659-661, 2008.
Shohet et al., *Circulation*, 101(22):2554-2556, 2000.
Szoka and Papahadjopoulos, *Proc. Natl. Acad. Sci. USA*, 75:4194-4198, 1978.

What is claimed is:

1. A pharmaceutical composition comprising xenon-loaded echogenic liposomes and tPA, wherein the pharmaceutical composition comprises at least two different liposomes.

2. The composition of claim 1, wherein the composition comprises both the xenon-loaded echogenic liposomes, and wherein the tPA is comprised in a second liposome.

3. The composition of claim 2, wherein the second liposome is essentially free of xenon.

4. The composition of claim 2, wherein the xenon-loaded echogenic liposomes and the second liposomes are comprised in a slurry.

* * * * *